US008002987B2

(12) United States Patent
Kim et al.

(10) Patent No.: US 8,002,987 B2
(45) Date of Patent: Aug. 23, 2011

(54) STATIONARY PHASE AND COLUMN USING CUCURBITURIL BONDED SILICA GEL, AND SEPARATION METHOD OF TAXOL USING THE COLUMN

(75) Inventors: Kimoon Kim, Pohang (KR);
Kyeng-Min Park, Pohang (KR);
Young-Ho Ko, Pohang (KR);
Narayanan Selvapalam, Pohang (KR);
Erumaipatty R Nagarajan, Pohang (KR)

(73) Assignee: Postech Academy-Industry Foundation, Kyungsangbuk-do (KR)

( * ) Notice: Subject to any disclaimer, the term of this patent is extended or adjusted under 35 U.S.C. 154(b) by 743 days.

(21) Appl. No.: 12/092,663

(22) PCT Filed: Mar. 24, 2006

(86) PCT No.: PCT/KR2006/001096
§ 371 (c)(1),
(2), (4) Date: May 5, 2008

(87) PCT Pub. No.: WO2007/111390
PCT Pub. Date: Oct. 4, 2007

(65) Prior Publication Data
US 2008/0290028 A1    Nov. 27, 2008

(51) Int. Cl.
*B01D 15/08* (2006.01)
(52) U.S. Cl. ............... 210/635; 210/656; 210/198.2; 210/502.1; 549/510
(58) Field of Classification Search ......... 210/635, 210/656, 659, 198.2, 502.1; 549/510
See application file for complete search history.

(56) References Cited

U.S. PATENT DOCUMENTS

| | | | | |
|---|---|---|---|---|
| 5,279,949 A * | 1/1994 | Nair | ............... | 435/123 |
| 5,478,736 A * | 12/1995 | Nair | ............... | 435/123 |
| 5,480,639 A * | 1/1996 | ElSohly et al. | ............ | 424/770 |
| 5,969,165 A * | 10/1999 | Liu | ............... | 549/510 |
| 6,639,069 B2 | 10/2003 | Kim et al. | | |
| 6,878,832 B2 * | 4/2005 | Saiji | ............... | 549/510 |
| 2004/0063977 A1 * | 4/2004 | Saiji | ............... | 549/510 |
| 2006/0074254 A1 * | 4/2006 | Zhang et al. | ............... | 549/510 |

FOREIGN PATENT DOCUMENTS

WO     2004072151 A      8/2004
WO     WO 2004/072151  *   8/2004

(Continued)

OTHER PUBLICATIONS

Supplementary European Search Report dated Jan. 20, 2010.

(Continued)

*Primary Examiner* — Ernest G Therkorn
(74) *Attorney, Agent, or Firm* — Perman & Green, LLP

(57) ABSTRACT

Provided are a stationary phase and a column using a cucurbituril-bound silica gel, and a method of separating taxane using the column. The taxane separation method includes: preparing a column for taxane separation, the column being packed with a stationary phase including a cucurbituril-bound silica gel in which a cucurbituril represented by Formula 1 or 2 is covalently bound to a modified silica gel represented by Formula 3; dissolving a taxane powder in a solvent to prepare a taxane-containing solution; applying the taxane-containing solution to the column; supplying a mobile-phase solvent to the column to obtain a taxane extract from the column; and purifying taxane from the taxane extract. Therefore, highly purified taxane can be separated from a low-purity crude taxane extract.

14 Claims, 5 Drawing Sheets

FOREIGN PATENT DOCUMENTS

| | | |
|---|---|---|
| WO | 2004083176 A2 | 9/2004 |
| WO | 2005087777 A | 9/2005 |

OTHER PUBLICATIONS

Jae Wook Lee, S. Samal, N. Selvapalam, Hee-Joon Kim, and Kimoon Kim, Cucurbituril Homologues and Derivatives: New Opportunities in Supramolecular Chemistry, Feb. 12, 2003, pp. 621-630, vol. 36, No. 8, 2003, Accounts of Chemical Research, Pohang, Republic of Korea.

Mikhail V. Rekharsky, Tadashi Mori, Cheng Yang, Young Ho Ko, N. Selvapalam, Hyunuk Kim, David Sobransingh, Angel E. Kaifer, Simin Liu, Lyle Isaacs, Wei Chen, Sarvin Moghaddam, Michael K. Gilson, Kimoon Kim, and Yoshihisa Inoue, A Synthetic host-guest system achieves avidin-biotin affinity by overcoming enthalpy-entropy compensation, Dec. 26, 2007, pp. 20737-20742, vol. 104, No. 52, The National Academy of Sciences of the USA.

Kimoon Kim, Narayanan Selvapalam, Young Ho Ko, Kyeng Min Park, Dongwoo Kim, and Jeeyeon Kim, Functionalized cucurbiturils and their applications, Nov. 7, 2006, pp. 267-279, 36, Chemical Society Reviews, The Royal Society of Chemistry 2007.

Youngkook Kim, Hyunuk Kim, Young Ho Ko, Narayanan Selvapalam, Mikhail V. Rekharsky, Yoshihisa Inoue, and Kimoon Kim, Complexation of Aliphatic Ammonium Ions with a Water-Soluble Cucurbit[6]uril Derivative in Pure Water: Isothermal Calorimetric, NMR, and X-ray Crystallographic Study, 2009, pp. 6143-6151, Chem. Eur. J.

\* cited by examiner

STATIONARY PHASE AND COLUMN USING CUCURBITURIL BONDED SILICA GEL, AND SEPARATION METHOD OF TAXOL USING THE COLUMN

CROSS-REFERENCE TO RELATED APPLICATIONS

This application is the National Stage of International Application No. PCT/KR2006/001096, International Filing Date, 24 Mar. 2006, which designated the United States of America, and which international application was published under PCT Article 21(2) as WO Publication No. WO 2007/111390 A1.

TECHNICAL FIELD

The present invention relates to a stationary phase and a column using a cucurbituril-bound silica gel, and a method of separating taxane using the column. More particularly, the present invention relates to a stationary phase and a column that achieve highly purified taxane at low costs, and a method of separating taxane using the column.

BACKGROUND ART

Paclitaxel has been approved as one of the most important anticancer drugs over the last 15 years. Natural products (e.g., paclitaxel), called "taxanes", are known as therapeutic drugs for cancer-associated diseases, and their applications have been expanded to many other drugs. Paclitaxel is a natural taxane extracted from the bark of the Pacific yew tree (*Taxus Brevifolia*). In addition, taxanes are derived from *Taxus baccata, Taxus canadensis, Taxus wallichiana, Taxus yunnanensis, Taxus densiformis, Taxus hicksii, Taxus wardii, Taxus cuspidata, Taxus capitata, Taxus brownie*, etc. [Miller et al. J. Org. Chem., 46: 1469 (1981); McLaughlin et al. J. Nat. Prod., 44: 321 (1981); Kingston et al. J. Nat. Prod., 45: 466 (1982)].

Taxanes are also derived from in-vitro cultured plant cells (U.S. Pat. Nos. 5,019,504; 5,637,484; 5,665,576; 5,871,979), fungi (U.S. Pat. No. 5,322,779), bacteria (U.S. Pat. No. 5,561,055), etc.

Taxanes, i.e., crude taxane extracts were tested for drug screening in 1960. An effective ingredient (paclitaxel) of a crude taxane extract was separated by Wani et al. in 1971, and the chemical structure of paclitaxel was identified by the same group. Paclitaxel has a potent, broad-spectrum anticancer activity in animal models of solid tumors, melanoma, leukemia, various cancers, sarcomas, and non-Hodgkin lymphomas. Clinical trials using paclitaxel have demonstrated that paclitaxel-containing drugs have potent cancer-combating properties. Thus, paclitaxel (Taxol™) and its semisynthetic analogue, docetaxel (Taxotere™) have been used alone or in combination with other drug(s), such as cisplatin, for the treatment of ovarian cancer, breast cancer, and non-small-cell lung cancer.

The analysis of paclitaxel and other taxanes is performed mainly by reverse-phase High-Performance Liquid Chromatography (reverse-phase HPLC), although other methods such as multimodal thin layer chromatography, micellar electrokinetic chromatography, tandem mass spectrometry, and gas chromatography have been reported. Reverse-phase HPLC is more effective in yielding taxane crystals, and the HPLC-based separation of taxanes from both plant materials and biological fluids was recently reported by Theodoridis, et al. [Phytochem. Anal. 7: 169-184, 1996]. In order to effectively separate taxane from a taxane mixture, there has been used an HPLC column packed with silica, alumina, an alkyl (e.g., C18 and C8)—functionalized silica resin, or a polystyrene divinylbenzene resin. For the purpose of appropriate separation of taxanes, researchers have developed silica gels modified with a diversely functionalized alkyl chain, such as a phenyl-, biphenyl-, pentafluorophenyl-, or cyano-modified silica gel. Ketchum, et al. [J. Liq. Chromatogr. 16: 2519-2530, 1993] investigated a separation efficiency of taxanes according to the type of a stationary phase column. Furthermore, a polyfluorinated reverse-phase column for taxane separation was recently reported [Anal. Chim. Acta., 319: 187-190, 1996]. As a result of intensive research on a column material, some companies have developed various silica-based columns, such as Phenomenex, Curosil, Whatman TAC1, Metachem Taxil, and Zorbax SW-Taxane. However, some of these columns are more suitable for bark extracts, and some other columns are more suitable for needle extracts. More recently, a polymer-coated silica material for taxane separation was developed (PCT International Publication No. WO 2004/083176).

However, the above-described techniques have some limitations in terms of purification costs and product purity. Therefore, a taxane purification technique capable of reducing purification costs and increasing taxane purity is needed.

DETAILED DESCRIPTION OF THE INVENTION

Technical Goal of the Invention

Figure 1:
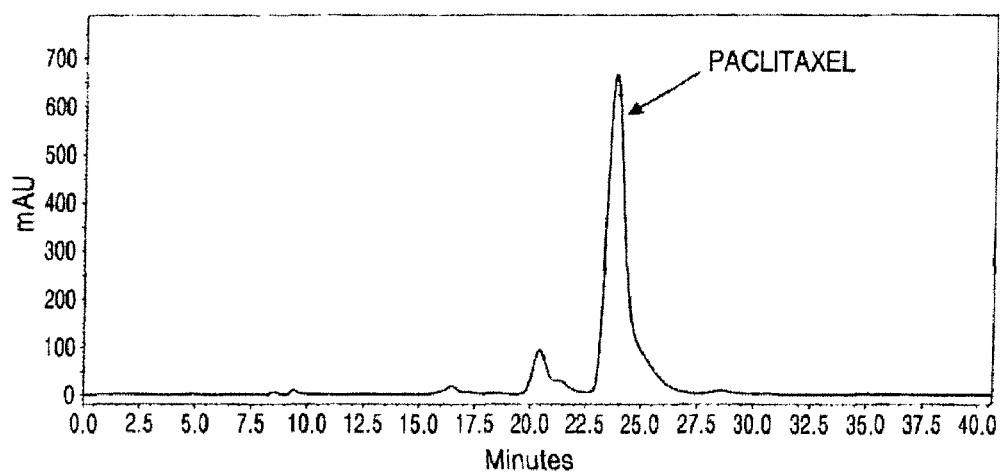
FIG. 1 is an HPLC pattern of paclitaxel separated from a crude extract (paclitaxel purity: 62.9 wt %) derived from a yew tree according to Example 4.

The present invention provides a stationary phase for taxane separation using a cucurbituril-bound silica gel to achieve highly purified taxane at low costs.

The present invention also provides a column for taxane separation including the stationary phase to achieve highly purified taxane at low costs.

The present invention also provides a method of separating taxane using the column to achieve highly purified taxane at low costs.

Disclosure of the Invention

According to an aspect of the present invention, there is provided a stationary phase for taxane separation, including a cucurbituril-bound silica gel in which a cucurbituril represented by Formula 1 or 2 below is covalently bound to a modified silica gel represented by Formula 3 below:

<Formula 1>

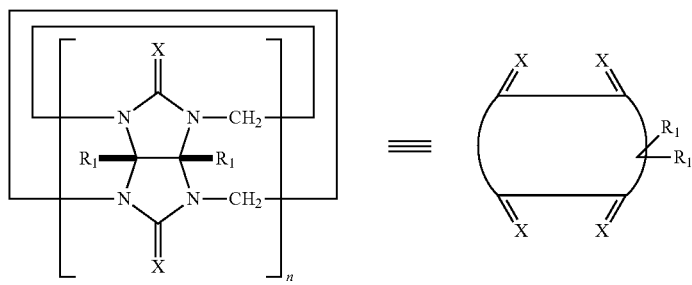

wherein at least one of $R_1$'s is selected from the group consisting of hydrogen, a hydroxy group, a substituted or unsubstituted alkyloxy group of C1-C30, a substituted or unsubstituted alkenyloxy group of C1-C30, a substituted or unsubstituted alkynyloxy group of C1-C30, a substituted or unsubstituted carbonylalkyloxy group of C2-C30, a substituted or unsubstituted thioalkyloxy group of C1-C30, a substituted or unsubstituted alkylthioloxy group of C1-C30, a substituted or unsubstituted hydroxyalkyloxy group of C1-C30, a substituted or unsubstituted alkylsiloxy group of C1-C30, a substituted or unsubstituted aminoalkyloxy group of C1-C30, a substituted or unsubstituted aminoalkylthiolalkyloxy group of C1-C30, a substituted or unsubstituted cycloalkyloxy group of C5-C30, a substituted or unsubstituted heterocycloalkyloxy group of C2-C30, a substituted or unsubstituted aryloxy group of C6-C30, a substituted or unsubstituted arylalkyloxy group of C6-C20, a substituted or unsubstituted heteroaryloxy group of C4-C30, a substituted or unsubstituted heteroarylalkyloxy group of C4-C30, a substituted or unsubstituted alkylthio group of C1-C30, a substituted or unsubstituted alkenylthio group of C1-C30, a substituted or unsubstituted alkynylthio group of C1-C30, a substituted or unsubstituted carbonylalkylthio group of C2-C30, a substituted or unsubstituted thioalkylthio group of C1-C30, a substituted or unsubstituted hydroxyalkylthio group of C1-C30, a substituted or unsubstituted alkylsilylthio group of C1-C30, a substituted or unsubstituted aminoalkylthio group of C1-C30, a substituted or unsubstituted aminoalkylthiolalkylthio group of C1-C30, a substituted or unsubstituted cycloalkylthio group of C5-C30, a substituted or unsubstituted heterocycloalkylthio group of C2-C30, a substituted or unsubstituted arylthio group of C6-C30, a substituted or unsubstituted arylalkylthio group of C6-C20, a substituted or unsubstituted heteroarylthio group of C4-C30, a substituted or unsubstituted heteroarylalkylthio group of C4-C30, a substituted or unsubstituted alkylamine group of C1-C30, a substituted or unsubstituted alkenylamine group of C1-C30, a substituted or unsubstituted alkynylamine group of C1-C30, a substituted or unsubstituted carbonylalkylamine group of C2-C30, a substituted or unsubstituted thioalkylamine group of C1-C30, a substituted or unsubstituted hydroxyalkylamine group of C1-C30, a substituted or unsubstituted alkylsilylamine group of C1-C30, a substituted or unsubstituted trialkyloxysilyl alkyl-carbamate group of C1-C30, a substituted or unsubstituted trialkyloxysilyl alkyl-thiocarbamate group of C1-C30, a substituted or unsubstituted trialkyloxysilyl alkyloxy group of C1-C30, a substituted or unsubstituted trialkyloxysilyl alkyl-carbonyloxy group of C1-C30, a substituted or unsubstituted trialkyloxysilyl heteroalkyl-alkyloxy group of C1-C30, a substituted or unsubstituted aminoalkylamine group of C1-C30, a substituted or unsubstituted aminoalkylthiolalkylamine group of C1-C30, a substituted or unsubstituted cycloalkylamine group of C5-C30, a substituted or unsubstituted heterocycloalkylamine group of C2-C30, a substituted or unsubstituted arylamine group of C6-C30, a substituted or unsubstituted arylalkylamine group of C6-C20, a substituted or unsubstituted heteroarylamine group of C4-C30, a substituted or unsubstituted heteroarylalkylamine group of C4-C30, a substituted or unsubstituted alkylazide group of C1-C30, a substituted or unsubstituted arylazide group of C1-C30, a substituted or unsubstituted alkylcarboxylazide group of C1-C30, and a substituted or unsubstituted arylcarboxylazide group of C1-C30;

X is O, S, or NH; and n is an integer of 4 to 20,

<Formula 2>

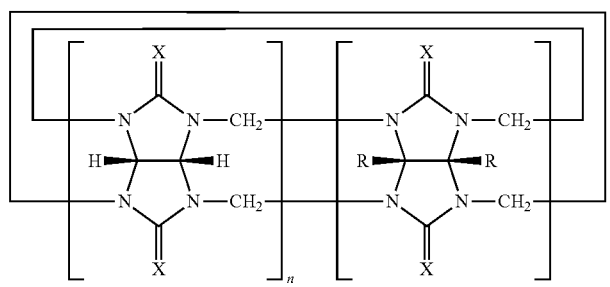

wherein at least one of R's is selected from the group consisting of hydrogen, a hydroxy group, a substituted or unsubstituted alkyloxy group of C1-C30, a substituted or unsubstituted alkenyloxy group of C1-C30, a substituted or unsubstituted alkynyloxy group of C1-C30, a substituted or unsubstituted carbonylalkyloxy group of C2-C30, a substituted or unsubstituted thioalkyloxy group of C1-C30, a substituted or unsubstituted alkylthioloxy group of C1-C30, a substituted or unsubstituted hydroxyalkyloxy group of C1-C30, a substituted or unsubstituted alkylsiloxy group of C1-C30, a substituted or unsubstituted aminoalkyloxy group of C1-C30, a substituted or unsubstituted aminoalkylthiolalkyloxy group of C1-C30, a substituted or unsubstituted cycloalkyloxy group of C5-C30, a substituted or unsubstituted heterocycloalkyloxy group of C2-C30, a substituted or unsubstituted aryloxy group of C6-C30, a substituted or unsubstituted arylalkyloxy group of C6-C20, a substituted or unsubstituted heteroaryloxy group of C4-C30, a substituted or unsubstituted heteroarylalkyloxy group of C4-C30, a substituted or unsubstituted alkylthio group of C1-C30, a substituted or unsubstituted alkenylthio group of C1-C30, a substituted or unsubstituted alkynylthio group of C1-C30, a substituted or unsubstituted carbonylalkylthio group of C2-C30, a substituted or unsubstituted thioalkylthio group of C1-C30, a substituted or unsubstituted hydroxyalkylthio group of C1-C30, a substituted or unsubstituted alkylsilylthio group of C1-C30, a substituted or unsubstituted aminoalkylthio group of C1-C30, a substituted or unsubstituted aminoalkylthiolalkylthio group of C1-C30, a substituted or unsubstituted cycloalkylthio group of C5-C30, a substituted or unsubstituted heterocycloalkylthio group of C2-C30, a substituted or unsubstituted arylthio group of C6-C30, a substituted or unsubstituted arylalkylthio group of C6-C20, a substituted or unsubstituted heteroarylthio group of C4-C30, a substituted or unsubstituted heteroarylalkylthio group of C4-C30, a substituted or unsubstituted alkylamine group of C1-C30, a substituted or unsubstituted alkenylamine group of C1-C30, a substituted or unsubstituted alkynylamine group of C1-C30, a substituted or unsubstituted carbonylalkylamine group of C2-C30, a substituted or unsubstituted thioalkylamine group of C1-C30, a substituted or unsubstituted hydroxyalkylamine group of C1-C30, a substituted or unsubstituted alkylsilylamine group of C1-C30, a substituted or unsubstituted trialkyloxysilyl alkyl-carbamate group of C1-C30, a substituted or unsubstituted trialkyloxysilyi alkyl-thiocarbamate group of C1-C30, a substituted or unsubstituted trialkyloxysilyl alkyloxy group of C1-C30, a substituted or unsubstituted trialkoxysilyl alkyl-carbonyloxy group of C1-C30, a substituted or unsubstituted trialkyloxysilyi heteroalkyl-alkyloxy group of C1-C30, a substituted or unsubstituted aminoalkylamine group of C1-C30, a substituted or unsubstituted aminoalkylthiolalkylamine group of C1-C30, a substituted or unsubstituted cycloalkylamine group of C5-C30, a substituted or unsubstituted heterocycloalkylamine group of C2-C30, a substituted or unsubstituted arylamine group of C6-C30, a substituted or unsubstituted arylalkylamine group of C6-C20, a substituted or unsubstituted heteroarylamine group of C4-C30, a substituted or unsubstituted heteroarylalkylamine group of C4-C30, a substituted or unsubstituted alkylazide group of C1-C30, a substituted or unsubstituted arylazide group of C1-C30, a substituted or unsubstituted alkylcarboxylazide group of C1-C30, and a substituted or unsubstituted arylcarboxylazide group of C1-C30;

X is O, S, or NH; and n is an integer of 3 to 19, and

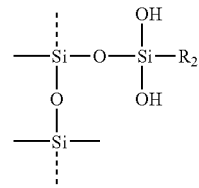

<Formula 3> wherein $R_2$ is an alkylthiol group with an alkyl moiety of C2-C10, an alkylamine group with an alkyl moiety of C2-C10, an epoxyalkyloxyalkyl group with an alkyl moiety of C2-C10, an isocyanatoalkyl group with an alkyl moiety of C2-C10, a halogenated alkyl group with an alkyl moiety of C2-C10, or a hydroxy group.

The cucurbituril of Formula 1 or 2 above may be covalently bound to the modified silica gel of Formula 3 above via a silane linker represented by Formula 4 below:

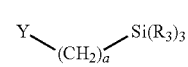

<Formula 4> wherien Y is selected from the group consisting of a thiol group, an amino group, an epoxy group, an isocyanate group, an isothiocyanate group, a hydroxy group, a carboxylated halogen, an azide group, an alkenyloxy group, a carbonylalkyloxy group, a thioalkyloxy group, an alkylthioloxy group, a hydroxyalkyloxy group, an alkylsilyloxy group, an aminoalkyloxy group, an aminoalkylthiolalkyloxy group, a cycloalkyloxy group, a heterocycloalkyloxy group, an aryloxy group, an arylalkyloxy group, a heteroaryloxy group, a heteroarylalkyloxy group, an alkylthio group, an alkenylthio group, an alkynylthio group, a carbonylalkylthio group, a thioalkylthio group, a hydroxyalkylthio group, an alkylsilylthio group, an aminoalkylthio group, an aminoalkylthiolalkylthio group, a cycloalkylthio group, a heterocycloalkylthio group, an arylthio group, an arylalkylthio group, a heteroarylthio group, a heteroarylalkylthio group, an alkylamine group, an alkenylamine group, an alkynylamine group, a carbonylalkylamine group, a thioalkylamine group, a hydroxyalkylamine group, an alkylsilylamine group, an aminoalkylamine group, an aminoalkylthiolalkylamine group, a cycloalkylamine group, a heterocycloalkylamine group, an arylamine group, an arylalkylamine group, a heteroarylamine group, and a heteroarylalkylamine group;

a is an integer of 1 to 10; and $R_3$ is selected from the group consisting of hydrogen, a halogen atom, an allyl group, an alkyl group of C1-C20, a halogenated alkyl group of C1-C20, and an alkyloxy group of C1-C20.

In Formula 4 above, $R_3$ may be —$OC_2H_5$, Y may be NCO, and a may be 3.

The cucurbituril-bound silica gel may be represented by Formula 5 or 6 below:

<Formula 5>

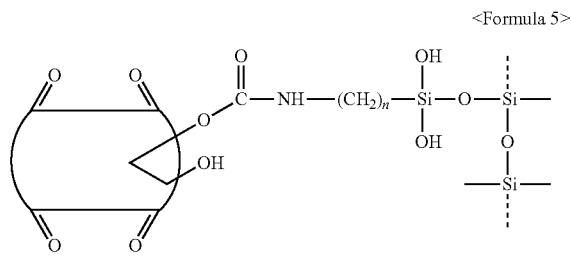

wherein n is an integer of 4 to 20, and

<Formula 6>

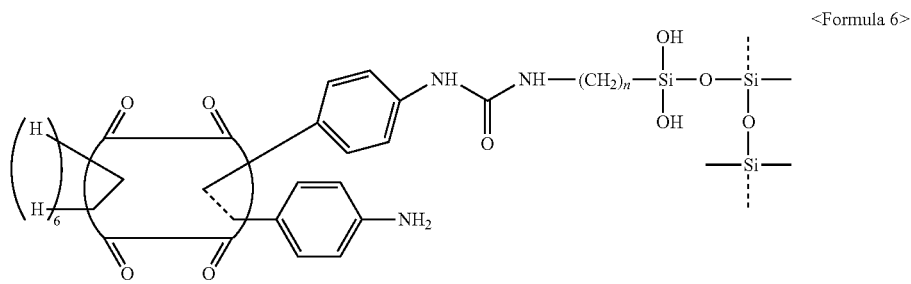

wherein n is an integer of 4 to 20.

In Formula 1 above, at least one of $R_1$'s may be selected from the group consisting of hydrogen, a hydroxy group, an aminophenyl group, an aryloxy group, a halomethyl group, and an aminoalkyl group of C1-C10, X may be O, and n may be 7. The halomethyl group may be a bromomethyl group, a fluoromethyl group, or an iodomethyl group.

In Formula 1 above, $R_1$'s may be each a hydroxy group.

In Formula 2 above, at least one of R's may be selected from the group consisting of hydrogen, a hydroxy group, an aminophenyl group, an aryloxy group, a halomethyl group, and an aminoalkyl group of C1-C10, X may be O, and n may be 6. The halomethyl group may be a bromomethyl group, a fluoromethyl group, or an iodomethyl group.

In Formula 2 above, R's may be each $C_6H_5$—$NH_2$.

In Formula 3 above, $R_2$ may be a hydroxy group.

According to another aspect of the present invention, there is provided a column for taxane separation, being packed with the above-described stationary phase.

According to still another aspect of the present invention, there is provided a method of separating taxane, the method including: preparing a column for taxane separation, the column being packed with a stationary phase including a cucurbituril-bound silica gel in which a cucurbituril represented by Formula 1 or 2 below is covalently bound to a modified silica gel represented by Formula 3 below; dissolving a taxane powder in a solvent to prepare a taxane-containing solution; applying the taxane-containing solution to the column; supplying a mobile-phase solvent to the column to obtain a taxane extract from the column; and purifying taxane from the taxane extract:

<Formula 1>

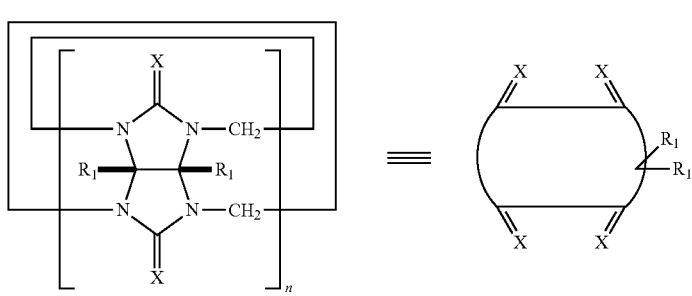

wherein at least one of $R_1$'s is selected from the group consisting of hydrogen, a hydroxy group, a substituted or unsubstituted alkyloxy group of C1-C30, a substituted or unsubstituted alkenyloxy group of C1-C30, a substituted or unsubstituted alkynyloxy group of C1-C30, a substituted or unsubstituted carbonylalkyloxy group of C2-C30, a substituted or unsubstituted thioalkyloxy group of C1-C30, a substituted or unsubstituted alkylthiooxy group of C1-C30, a substituted or unsubstituted hydroxyalkyloxy group of C1-C30, a substituted or unsubstituted alkylsiloxy group of C1-C30, a substituted or unsubstituted aminoalkyloxy group of C1-C30, a substituted or unsubstituted aminoalkylthiolalkyloxy group of C1-C30, a substituted or unsubstituted cycloalkyloxy group of C5-C30, a substituted or unsubstituted heterocycloalkyloxy group of C2-C30, a substituted or unsubstituted aryloxy group of C6-C30, a substituted or unsubstituted arylalkyloxy group of C6-C20, a substituted or unsubstituted heteroaryloxy group of C4-C30, a substituted or unsubstituted heteroarylalkyloxy group of C4-C30, a substituted or unsubstituted alkylthio group of C1-C30, a substituted or unsubstituted alkenylthio group of C1-C30, a substituted or unsubstituted alkynylthio group of C1-C30, a substituted or unsubstituted carbonylalkylthio group of C2-C30, a substituted or unsubstituted thioalkylthio group of C1-C30, a substituted or unsubstituted hydroxyalkylthio group of C1-C30, a substituted or unsubstituted alkylsilylthio group of C1-C30, a substituted or unsubstituted aminoalkylthio group of C1-C30, a substituted or unsubstituted aminoalkylthiolalkylthio group of C1-C30, a substituted or unsubstituted cycloalkylthio group of C5-C30, a substituted or unsubstituted heterocycloalkylthio group of C2-C30, a substituted or unsubstituted arylthio group of C6-C30, a substituted or unsubstituted arylalkylthio group of C6-C20, a substituted or unsubstituted heteroarylthio group of C4-C30, a substituted or unsubstituted heteroarylalkylthio group of C4-C30, a substituted or unsubstituted alkylamine group of C1-C30, a substituted or unsubstituted alkenylamine group of C1-C30, a substituted or unsubstituted alkynylamine group of C1-C30, a substituted or unsubstituted carbonylalkylamine group of C2-C30, a substituted or unsubstituted thioalkylamine group of C1-C30, a substituted or unsubstituted hydroxyalkylamine group of C1-C30, a substituted or unsubstituted alkylsilylamine group of C1-C30, a substituted or unsubstituted trialkyloxysilyl alkyl-carbamate group of C1-C30, a substituted or unsubstituted trialkyloxysilyl alkyl-thiocarbamate group of C1-30, a substituted or unsubstituted trialkyloxysilyl alkyloxy group of C1-C30, a substituted or unsubstituted trialkyloxysilyl alkyl-carbonyloxy group of C1-C30, a substituted or unsubstituted trialkyloxysilyl heteroalkyl-alkyloxy group of C1-C30, a substituted or unsubstituted aminoalkylamine group of C1-C30, a substituted or unsubstituted aminoalkylthiolalkylamine group of C1-C30, a substituted or unsubstituted cycloalkylamine group of C5-C30, a substituted or unsubstituted heterocycloalkylamine group of C2-C30, a substituted or unsubstituted arylamine group of C6-C30, a substituted or unsubstituted arylalkylamine group of C6-C20, a substituted or unsubstituted heteroarylamine group of C4-C30, a substituted or unsubstituted heteroarylalkylamine group of C4-C30, a substituted or unsubstituted alkylazide group of C1-C30, a substituted or unsubstituted arylazide group of C1-C30, a substituted or unsubstituted alkylcarboxylazide group of C1-C30, and a substituted or unsubstituted arylcarboxylazide group of C1-C30;

X is O, S, or NH; and n is an integer of 4 to 20,

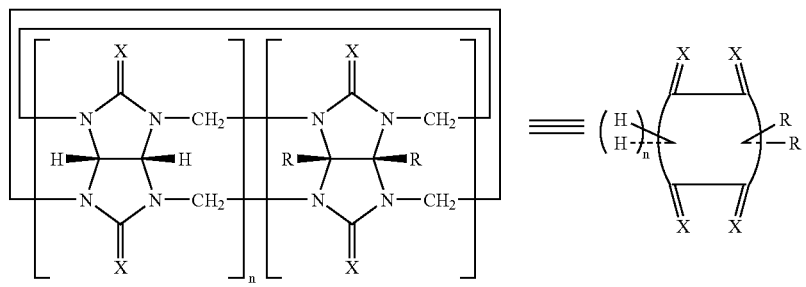

<Formula 2> wherein at least one of R's is selected from the group consisting of hydrogen, a hydroxy group, a substituted or unsubstituted alkyloxy group of C1-C30, a substituted or unsubstituted alkenyloxy group of C1-C30, a substituted or unsubstituted alkynyloxy group of C1-C30, a substituted or unsubstituted carbonylalkyloxy group of C2-C30, a substituted or unsubstituted thioalkyloxy group of C1-C30, a substituted or unsubstituted alkylthioloxy group of C1-C30, a substituted or unsubstituted hydroxyalkyloxy group of C1-C30, a substituted or unsubstituted alkylsiloxy group of C1-C30, a substituted or unsubstituted aminoalkyloxy group of C1-C30, a substituted or unsubstituted aminoalkylthiolalkyloxy group of C1-C30, a substituted or unsubstituted cycloalkyloxy group of C5-C30, a substituted or unsubstituted heterocycloalkyloxy group of C2-C30, a substituted or unsubstituted aryloxy group of C6-C30, a substituted or unsubstituted arylalkyloxy group of C6-C20, a substituted or unsubstituted heteroaryloxy group of C4-C30, a substituted or unsubstituted heteroarylalkyloxy group of C4-C30, a substituted or unsubstituted alkylthio group of C1-C30, a substituted or unsubstituted alkenylthio group of C1-C30, a substituted or unsubstituted alkynylthio group of C1-C30, a substituted or unsubstituted carbonylalkylthio group of C2-C30, a substituted or unsubstituted thioalkylthio group of C1-C30, a substituted or unsubstituted hydroxyalkylthio group of C1-C30, a substituted or unsubstituted alkylsilylthio group of C1-C30, a substituted or unsubstituted aminoalkylthio group of C1-C30, a substituted or unsubstituted aminoalkylthiolalkylthio group of C1-C30, a substituted or unsubstituted cycloalkylthio group of C5-C30, a substituted or unsubstituted heterocycloalkylthio group of C2-C30, a substituted or unsubstituted arylthio group of C6-C30, a substituted or unsubstituted arylalkylthio group of C6-C20, a substituted or unsubstituted heteroarylthio group of C4-C30, a substituted or unsubstituted heteroarylalkylthio group of C4-C30, a substituted or unsubstituted alkylamine group of C1-C30, a substituted or unsubstituted alkenylamine group of C1-C30, a substituted or unsubstituted alkynylamine group of C1-C30, a substituted or unsubstituted carbonylalkylamine group of C2-C30, a substituted or unsubstituted thioalkylamine group of C1-C30, a substituted or unsubstituted hydroxyalkylamine group of C1-C30, a substituted or unsubstituted alkylsilylamine group of C1-C30, a substituted or unsubstituted trialkyloxysilyl alkyl-carbamate group of C1-C30, a substituted or unsubstituted trialkyloxysilyl alkyl-thiocarbamate group of C1-C30, a substituted or unsubstituted trialkyloxysilyl alkyloxy group of C1-C30, a substituted or unsubstituted trialkyloxysilyl alkyl-carbonyloxy group of C1-C30, a substituted or unsubstituted trialkyloxysilyl heteroalkyl-alkyloxy group of C1-C30, a substituted or unsubstituted aminoalkylamine group of C1-C30, a substituted or unsubstituted aminoalkylthiolalkylamine group of C1-C30, a substituted or unsubstituted cycloalkylamine group of C5-C30, a substituted or unsubstituted heterocycloalkylamine group of C2-C30, a substituted or unsubstituted arylamine group of C6-C30, a substituted or unsubstituted arylalkylamine group of C6-C20, a substituted or unsubstituted heteroarylamine group of C4-C30, a substituted or unsubstituted heteroarylalkylamine group of C4-C30, a substituted or unsubstituted alkylazide group of C1-C30, a substituted or unsubstituted arylazide group of C1-C30, a substituted or unsubstituted alkylcarboxylazide group of C1-C30, and a substituted or unsubstituted arylcarboxylazide group of C1-C30;

X is O, S, or NH; and n is an integer of 3 to 19, and

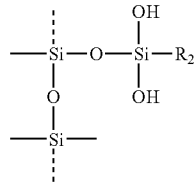

<Formula 3> wherein $R_2$ is an alkylthiol group with an alkyl moiety of C2-C10, an alkylamine group with an alkyl moiety of C2-C10, an epoxyalkyloxyalkyl group with an alkyl moiety of C2-C10, an isocyanatoalkyl group with an alkyl moiety of C2-C10, a halogenated alkyl group with an alkyl moiety of C2-C10, or a hydroxy group.

The cucurbituril of Formula 1 or 2 above may be covalently bound to the modified silica gel of Formula 3 above via a silane linker represented by Formula 4 below:

$$Y_{(CH_2)_a} Si(R_3)_3$$

<Formula 4> wherien Y is selected from the group consisting of a thiol group, an amino group, an epoxy group, an isocyanate group, an isothiocyanate group, a hydroxy group, a carboxylated halogen, an azide group, an alkenyloxy group, a carbonylalkyloxy group, a thioalkyloxy group, an alkylthioloxy group, a hydroxyalkyloxy group, an alkylsilyloxy group, an aminoalkyloxy group, an aminoalkylthiolalkyloxy group, a cycloalkyloxy group, a heterocycloalkyloxy group, an aryloxy group, an arylalkyloxy group, a heteroaryloxy group, a heteroarylalkyloxy group, an alkylthio group, an alkynylthio group, an alkynylthio group, a carbonylalkylthio group, a thioalkylthio group, a hydroxyalkylthio group, an alkylsilylthio group, an aminoalkylthio group, an aminoalkylthiolalkylthio group, a cycloalkylthio group, a heterocycloalkylthio group, an arylthio group, an arylalkylthio group, a heteroarylthio group, a heteroarylalkylthio group, an alkylamine group, an alkenylamine group, an alkynylamine group, a carbonylalkylamine group, a thioalkylamine group, a hydroxyalkylamine group, an alkylsilylamine group, an aminoalkylamine group, an aminoalkylthiolalkylamine group, a cycloalkylamine group, a heterocycloalkylamine group, an arylamine group, an arylalkylamine group, a heteroarylamine group, and a heteroarylalkylamine group;

a is an integer of 1 to 10; and $R_3$ is selected from the group consisting of hydrogen, a halogen atom, an allyl group, an alkyl group of C1-C20, a halogenated alkyl group of C1-C20, and an alkyloxy group of C1-C20.

In Formula 4 above, $R_3$ may be $-OC_2H_5$, Y may be NCO, and a may be 3.

The cucurbituril-bound silica gel may be represented by Formula 5 or 6 below:

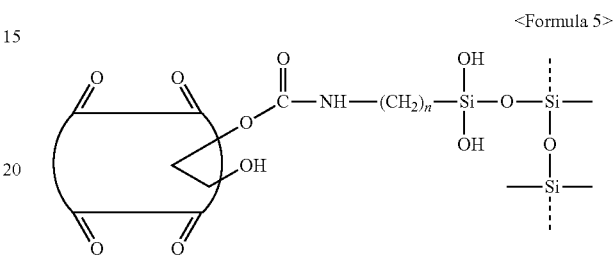

<Formula 5> wherein n is an integer of 4 to 20, and

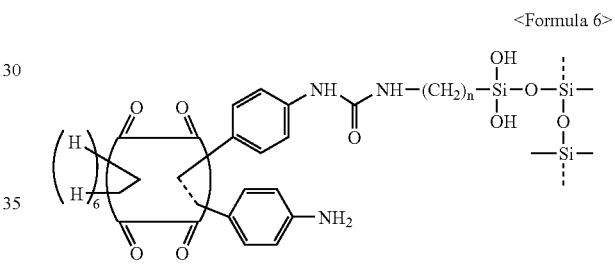

<Formula 6> wherein n is an integer of 4 to 20.

In the method of the present invention, the purification of the taxane from the taxane extract may include distilling the taxane extract under vacuum to obtain an organic solvent-free taxane concentrate and crystallizing the taxane concentrate.

The purification of the taxane from the taxane extract may further include lyophilizing the taxane concentrate after the crystallization.

Preferable examples of $R_1$'s of Formula 1 and R's of Formula 2 are as illustrated above.

Effect of the Invention

According to the present invention, a stationary phase for taxane separation using a cucurbituril-bound silica gel can reduce purification costs and increase the purity of taxane.

A column for taxane separation including the stationary phase can reduce purification costs and increase the purity of taxane.

A method of separating taxane using the column can achieve highly purified taxane at low costs.

BEST MODE FOR CARRYING OUT THE INVENTION

The present invention will now be described more fully with reference to the accompanying drawings, in which exemplary embodiments of the invention are shown.

The present invention provides a stationary phase for taxane separation, including a cucurbituril-bound silica gel in which a cucurbituril represented by Formula 1 or 2 below is covalently bound to a modified silica gel represented by Formula 3 below:

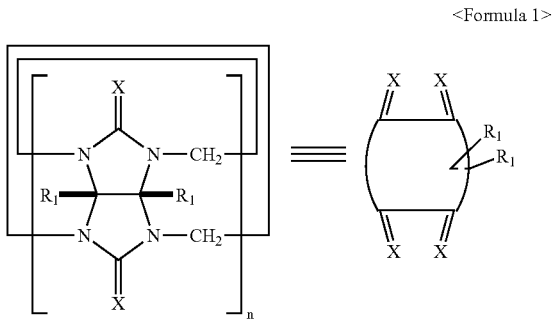

<Formula 1> wherein at least one of $R_1$'s is selected from the group consisting of hydrogen, a hydroxy group, a substituted or unsubstituted alkyloxy group of C1-C30, a substituted or unsubstituted alkenyloxy group of C1-C30, a substituted or unsubstituted alkynyloxy group of C1-C30, a substituted or unsubstituted carbonylalkyloxy group of C2-C30, a substituted or unsubstituted thioalkyloxy group of C1-C30, a substituted or unsubstituted alkylthioloxy group of C1-C30, a substituted or unsubstituted hydroxyalkyloxy group of C1-C30, a substituted or unsubstituted alkylsiloxy group of C1-C30, a substituted or unsubstituted aminoalkyloxy group of C1-C30, a substituted or unsubstituted aminoalkylthiolalkyloxy group of C1-C30, a substituted or unsubstituted cycloalkyloxy group of C5-C30, a substituted or unsubstituted heterocycloalkyloxy group of C2-C30, a substituted or unsubstituted aryloxy group of C6-C30, a substituted or unsubstituted arylalkyloxy group of C6-C20, a substituted or unsubstituted heteroaryloxy group of C4-C30, a substituted or unsubstituted heteroarylalkyloxy group of C4-C30, a substituted or unsubstituted alkylthio group of C1-C30, a substituted or unsubstituted alkenylthio group of C1-C30, a substituted or unsubstituted alkynylthio group of C1-C30, a substituted or unsubstituted carbonylalkylthio group of C2-C30, a substituted or unsubstituted thioalkylthio group of C1-C30, a substituted or unsubstituted arylthio group of C6-C30, a substituted or unsubstituted arylalkylthio group of C6-C20, a substituted or unsubstituted heteroarylthio group of C4-C30, a substituted or unsubstituted heteroarylalkylthio group of C4-C30, a substituted or unsubstituted alkylamine group of C1-C30, a substituted or unsubstituted alkenylamine group of C1-C30, a substituted or unsubstituted alkynylamine group of C1-C30, a substituted or unsubstituted carbonylalkylamine group of C2-C30, a substituted or unsubstituted thioalkylamine group of C1-C30, a substituted or unsubstituted hydroxyalkylamine group of C1-C30, a substituted or unsubstituted alkylsilylamine group of C1-C30, a substituted or unsubstituted trialkyloxysilyl alkyl-carbamate group of C1-C30, a substituted or unsubstituted trialkyloxysilyl alkyl-thiocarbamate group of C1-C30, a substituted or unsubstituted trialkyloxysilyl alkyloxy group of C1-C30, a substituted or unsubstituted trialkyloxysilyl alkyl-carbonyloxy group of C1-C30, a substituted or unsubstituted trialkyloxysilyl heteroalkyl-alkyloxy group of C1-C30, a substituted or unsubstituted aminoalkylamine group of C1-C30, a substituted or unsubstituted aminoalkylthiolalkylamine group of C1-C30, a substituted or unsubstituted cycloalkylamine group of C5-C30, a substituted or unsubstituted heterocycloalkylamine group of C2-C30, a substituted or unsubstituted arylamine group of C6-C30, a substituted or unsubstituted arylalkylamine group of C6-C20, a substituted or unsubstituted heteroarylamine group of C4-C30, a substituted or unsubstituted heteroarylalkylamine group of C4-C30, a substituted or unsubstituted alkylazide group of C1-C30, a substituted or unsubstituted arylazide group of C1-C30, a substituted or unsubstituted alkylcarboxylazide group of C1-C30, and a substituted or unsubstituted arylcarboxylazide group of C1-C30;

X is O, S, or NH; and n is an integer of 4 to 20.

As used herein, the $R_1$'s refer to $R_1$ groups of Formula 1.

At least one of $R_1$'s may be selected from the group consisting of hydrogen, a hydroxy group, an aminophenyl group, an allyloxy group, a halomethyl group, and an aminoalkyl group of C1-C10, X may be O, and n may be 7. More preferably, $R_1$'s may be each a hydroxy group.

The halomethyl group may be a bromomethyl group, a fluoromethyl group, or an iodomethyl group, but the present invention is not limited to the illustrated examples.

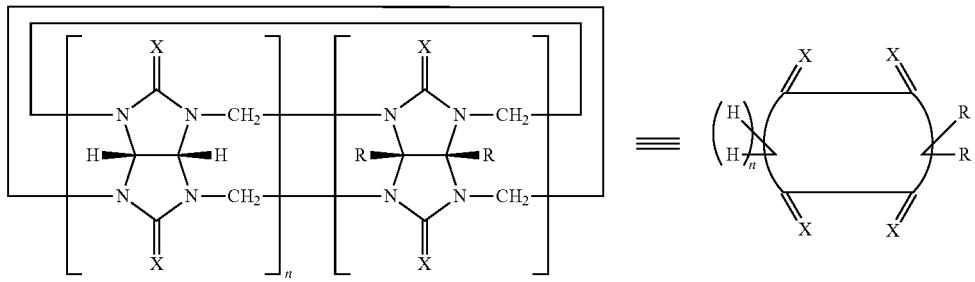

<Formula 2>

C1-C30, a substituted or unsubstituted hydroxyalkylthio group of C1-C30, a substituted or unsubstituted alkylsilylthio group of C1-C30, a substituted or unsubstituted aminoalkylthio group of C1-C30, a substituted or unsubstituted aminoalkylthiolalkylthio group of C1-C30, a substituted or unsubstituted cycloalkylthio group of C5-C30, a substituted or unsubstituted heterocycloalkylthio group of C2-C30, a wherein at least one of R's is selected from the group consisting of hydrogen, a hydroxy group, a substituted or unsubstituted alkyloxy group of C1-C30, a substituted or unsubstituted alkenyloxy group of C1-C30, a substituted or unsubstituted alkynyloxy group of C1-C30, a substituted or unsubstituted carbonylalkyloxy group of C2-C30, a substituted or unsubstituted thioalkyloxy group of C1-C30, a substituted or unsubstituted alkylthioloxy group of C1-C30, a substituted or unsubstituted hydroxyalkyloxy group of C1-C30, a substituted or unsubstituted alkylsiloxy group of C1-C30, a substituted or unsubstituted aminoalkyloxy group of C1-C30, a substituted or unsubstituted aminoalkylthiol alkyroxy group of C1-C30, a substituted or unsubstituted cycloalkyloxy group of C5-C30, a substituted or unsubstituted heterocycloalkyloxy group of C2-C30, a substituted or unsubstituted aryloxy group of C6-C30, a substituted or unsubstituted arylalkyloxy group of C6-C20, a substituted or unsubstituted heteroaryloxy group of C4-C30, a substituted or unsubstituted heteroarylalkyloxy group of C4-C30, a substituted or unsubstituted alkylthio group of C1-C30, a substituted or unsubstituted alkenylthio group of C1-C30, a substituted or unsubstituted alkynylthio group of C1-C30, a substituted or unsubstituted carbonylalkylthio group of C2-C30, a substituted or unsubstituted thioalkylthio group of C1-C30, a substituted or unsubstituted hydroxyalkylthio group of C1-C30, a substituted or unsubstituted alkylsilylthio group of C1-C30, a substituted or unsubstituted aminoalkylthio group of C1-C30, a substituted or unsubstituted aminoalkylthiolalkylthio group of C1-C30, a substituted or unsubstituted cycloalkylthio group of C5-C30, a substituted or unsubstituted heterocycloalkylthio group of C2-C30, a substituted or unsubstituted arylthio group of C6-C30, a substituted or unsubstituted arylalkylthio group of C6-C20, a substituted or unsubstituted heteroarylthio group of C4-C30, a substituted or unsubstituted heteroarylalkylthio group of C4-C30, a substituted or unsubstituted alkylamine group of C1-C30, a substituted or unsubstituted alkenylamine group of C1-C30, a substituted or unsubstituted alkynylamine group of C1-C30, a substituted or unsubstituted carbonylalkylamine group of C2-C30, a substituted or unsubstituted thioalkylamine group of C1-C30, a substituted or unsubstituted hydroxyalkylamine group of C1-C30, a substituted or unsubstituted alkylsilylamine group of C1-C30, a substituted or unsubstituted trialkyloxysilyl alkyl-carbamate group of C1-C30, a substituted or unsubstituted trialkyloxysilyl alkyl-thiocarbamate group of C1-C30, a substituted or unsubstituted trialkyloxysilyl alkyloxy group of C1-C30, a substituted or unsubstituted trialkyloxysilyl alkyl-carbonyloxy group of C1-C30, a substituted or unsubstituted trialkyloxysilyl heteroalkyl-alkyloxy group of C1-C30, a substituted or unsubstituted aminoalkylamine group of C1-C30, a substituted or unsubstituted aminoalkylthiolalkylamine group of C1-C30, a substituted or unsubstituted cycloalkylamine group of C5-C30, a substituted or unsubstituted heterocycloalkylamine group of C2-C30, a substituted or unsubstituted arylamine group of C6-C30, a substituted or unsubstituted arylalkylamine group of C6-C20, a substituted or unsubstituted heteroarylamine group of C4-C30, a substituted or unsubstituted heteroarylalkylamine group of C4-C30, a substituted or unsubstituted alkylazide group of C1-C30, a substituted or unsubstituted arylazide group of C1-C30, a substituted or unsubstituted alkylcarboxylazide group of C1-C30, and a substituted or unsubstituted arylcarboxylazide group of C1-C30;

X is O, S, or NH; and n is an integer of 3 to 19.

As used herein, the R's refer to R groups of Formula 2.

At least one of R's may be selected from the group consisting of hydrogen, a hydroxy group, an aminophenyl group, an allyloxy group, a halomethyl group, and an aminoalkyl group of C1-C10, X may be O, and n may be 6. More preferably, R's may be each $C_6H_5$—$NH_2$.

The halomethyl group may be a bromomethyl group, a fluoromethyl group, or an iodomethyl group, but the present invention is not limited to the illustrated examples.

Cucurbiturils were first reported by R. Behrend, E. Meyer, and F. Rusche in 1905. In early 2000, Ki-Moon Kim and coworkers reported the improved preparation and separation of well-known cucurbit[6]uril and its homologues, cucurbit[n]urils (n=5, 7, 8) and identified their X-ray crystal structures [*J. Am. Chem. Soc.* 2000, 122, 540].

The above-described cucurbiturils and cucurbituril derivatives are compounds consisting of unsubstituted glycoluril monomer units. Cucurbituril derivatives consisting of substituted glycoluril monomer units are also known [*Angew. Chem. Int. Ed. Engl.* 1992, 31, 1475]. Hereinafter, cucurbiturils and cucurbituril derivatives will be commonly referred to as simply "cucurbiturils".

Cucurbiturils are macrocyclic compounds and have a lipophilic cavity and two hydrophilic entrances at upper and lower portions. Thus, lipophilic interactions occur in the cavity of cucurbiturils, and hydrogen bonds, polar-polar interactions, and positive charge-polar interactions occur in the two entrances having six carbonyl groups. Therefore, cucurbiturils have retention capacity for various compounds by a very stable non-covalent linkage with these compounds. Cucurbiturils form a very stable non-covalent linkage, in particular, with compounds having a functional group such as an alkyl group, an amino group, or a carboxyl group, alkaline metals, heavy metals, or amine group-containing gaseous compounds. Based on such characteristics, studies about application of cucurbiturils in various areas have been continuously conducted.

Cucurbiturils are host molecules having cavities therein, and can form a non-covalent linkage with guest molecules to produce host-guest complexes [Acc. Chem. Res. 2003, 36, 621]. Furthermore, cucurbiturils also have adsorption capability to various molecules capable of non-covalently binding with the cucurbiturils, and harmful gases, such as CO and NOx, [*Angew. Chem. Int. Ed.* 2002, 41, 3020]. Thus, cucurbiturils can be used to filter out specific molecules or gas components.

Hydroxycucurbiturils and their mother cucurbiturils are disclosed, together with their chemical structures and synthetic methods, in Korean Patent Application Nos. 02-68362, 02-318, 01-57573, 01-39756, and 00-33026, filed by the present applicants, the disclosures of which are incorporated herein by reference in their entireties.

<Formula 3>

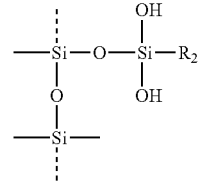

wherein $R_2$ is an alkylthiol group with an alkyl moiety of C2-C10, an alkylamine group with an alkyl moiety of C2-C10, an epoxyalkyloxyalkyl group with an alkyl moiety of C2-C10, an isocyanatoalkyl group with an alkyl moiety of C2-C10, a halogenated alkyl group with an alkyl moiety of C2-C10, or a hydroxy group.

The modified silica gel of Formula 3 above can be prepared by a synthesis method known in the art [U.S. Pat. No. 4,539,399; J. Chromatogr. 628 (1993) 11; Tetrahedron Lett. 26 (1985) 3361].

For example, the modified silica gel of Formula 3 above can be synthesized by reacting a silane having an end functional group, such as a thiol group, an amine group, an isocyanato group, or an epoxy group, with an uncoated silica gel used for column purification.

The cucurbituril-bound silica gel of the present invention can be synthesized by covalently binding the cucurbituril derivative of Formula 1 or 2 above with the modified silica gel of Formula 3 above. That is, the cucurbituril of Formula 1 or 2 above can be covalently bound to the modified silica gel of Formula 3 above by reacting an end functional group of $R_1$ or R of the cucurbituril, such as a carboxy group, an amino group, a hydroxy group, or an allyl group, with an end functional group of $R_2$ of the modified silica gel, such as an amino group, an epoxy group, an isocyanato group, or a thiol group [PCT International Publication Nos. WO 2004/072151 and WO 2005/010058].

The cucurbituril-bound silica gel of the present invention can also be synthesized by covalently binding the cucurbituril of Formula 1 or 2 above with the modified silica gel of Formula 3 above via a silane linker represented by Formula 4 below [PCT International Publication Nos. WO 2004/072151 and WO 2005/010058]. That is, the cucurbituril-bound silica gel of the present invention can be synthesized by binding the cucurbituril of Formula 1 or 2 above with the silane compound of Formula 4 below and binding the resultant product with the silica gel of Formula 3 above. In this case, $R_2$ of Formula 3 may be a hydroxy group.

<Formula 4>

wherien Y is selected from the group consisting of a thiol group, an amino group, an epoxy group, an isocyanate group, an isothiocyanate group, a hydroxy group, a carboxylated halogen, an azide group, an alkenyloxy group, a carbonylalkyloxy group, a thioalkyloxy group, an alkylthioloxy group, a hydroxyalkyloxy group, an alkylsilyloxy group, an aminoalkyloxy group, an aminoalkylthiolalkyloxy group, a cycloalkyloxy group, a heterocycloalkyloxy group, an aryloxy group, an arylalkyloxy group, a heteroaryloxy group, a heteroarylalkyloxy group, an alkylthio group, an alkenylthio group, an alkynylthio group, a carbonylalkylthio group, a thioalkylthio group, a hydroxyalkylthio group, an alkylsilylthio group, an aminoalkylthio group, an aminoalkylthiolalkylthio group, a cycloalkylthio group, a heterocycloalkylthio group, an arylthio group, an arylalkylthio group, a heteroarylthio group, a heteroarylalkylthio group, an alkylamine group, an alkenylamine group, an alkynylamine group, a carbonylalkylamine group, a thioalkylamine group, a hydroxyalkylamine group, an alkylsilylamine group, an aminoalkylamine group, an aminoalkylthiolalkylamine group, a cycloalkylamine group, a heterocycloalkylamine group, an arylamine group, an arylalkylamine group, a heteroarylamine group, and a heteroarylalkylamine group;

a is an integer of 1 to 10; and $R_3$ is selected from the group consisting of hydrogen, a halogen atom, an allyl group, an alkyl group of C1-C20, a halogenated alkyl group of C1-C20, and an alkyloxy group of C1-C20.

In Formula 4 above, $R_3$ may be —$OC_2H_5$, Y may be NCO, and a may be 3.

The present invention also provides a column for taxane separation, being packed with the above-prepared stationary phase.

In the present invention, a taxane source is selected from plant species, commonly called "yew tree", and plant cell culture extracts. Here, the plant cell culture extracts may be cell suspensions derived from Taxus chinensis.

As used herein, the term "taxane or taxane molecule" refers to a compound containing, but not limited to, a base baccatin III, or its isomer, homologue, or analogue.

The present invention also provides a method of separating paclitaxel and its natural analogues represented by the following formulae using the column for taxane separation:

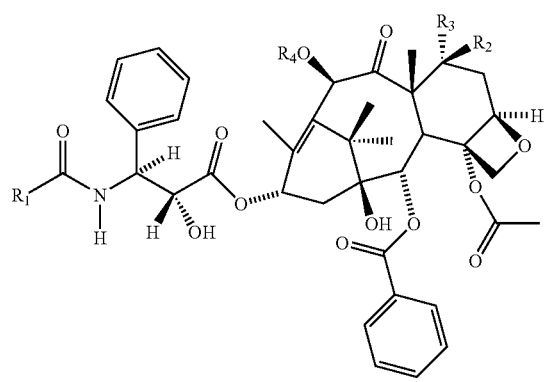

paclitaxel: $R_1$=Ph, $R_2$=OH, $R_3$=H, $R_4$=$CH_3CO$
10-deacetyltaxol: $R_1$=Ph, $R_2$=OH, $R_3$=H, $R_4$=H
7-epitaxol: $R_1$=Ph, $R_2$=H, $R_3$=OH, $R_4$=$CH_3CO$
cephalomanine: $R_1$=$CH_3$—CH=C($CH_3$), $R_2$=OH, $R_3$=H, $R_4$=$CH_3CO$
taxol C: $R_1$=$C_5H_{11}$, $R_2$=OH, $R_3$=H, $R_4$=$CH_3CO$
7-epi-10-deacetyltaxol: $R_1$=Ph, $R_2$=H, $R_3$=OH, $R_4$=H

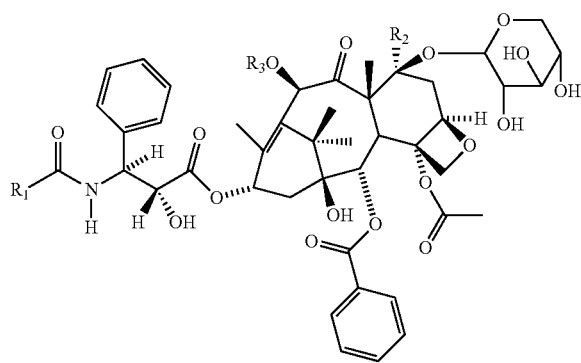

7-siloxyltaxol: $R_1$=Ph, $R_2$=H, $R_3$=$CH_3CO$
7-siloxyl-10-deacetyltaxol: $R_1$=Ph, $R_2$=H, $R_3$=H
7-siloxyl-10-deacetyltaxol C: $R_1$=$C_5H_{11}$, $R_2$=H, $R_3$=H
7-siloxyl-10-deacetyl cephalomanine: $R_1$=$CH_3$—CH=C($CH_3$), $R_2$=H, $R_3$=H

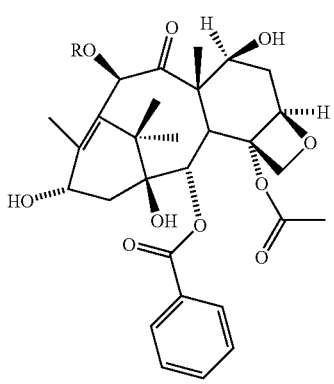

baccatin III: R=CH₃CO
10-deacetylbaccatin III: R=H

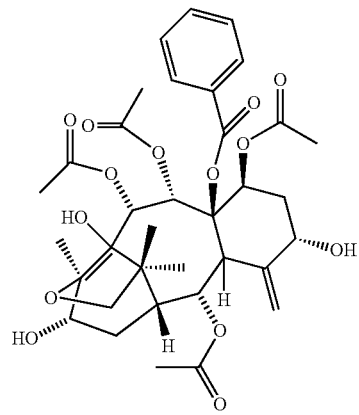

taxinine M

That is, the present invention provides a method of separating taxane compounds (including paclitaxel). In detail, paclitaxel analogues and homologues are separated in high purity from Taxus species or other sources by means of a cucurbituril-bound silica gel column. The cucurbituril-bound silica gel column may be a High Performance Liquid Chromatography (HPLC) column. Therefore, paclitaxel analogues can be separated from natural biomass extracts, products made in the semisynthetic or synthetic process for the taxane family, etc.

In order to purify paclitaxel and other taxane compounds from crude extracts, it is common to use an HPLC column containing silica, alumina, C8, C18, polystyrene divinylbenzene, or other material. In the present invention, in order to enhance the separation efficiency of paclitaxel and other taxane compounds, a column for taxane separation is used. As used herein, the term "column for taxane separation" refers to an HPLC column containing a cucurbituril-bound silica gel.

In the present invention, examples of a starting material of a cucurbituril-bound silica gel used in a stationary phase or a column for taxane separation include, but are not limited to, (1) a crude extract including paclitaxel or at least one taxane synthesized or semisynthesized from an intermediate such as baccatin III; (2) a crude extract including at least one taxane prepared from a preliminary chromatography column such as silica, alumina, C8, C18, or a polymer; (3) a crude extract including at least one taxane prepared by another preliminary chromatography; (4) a crude extract including taxane prepared by solvent partitioning, centrifugation, filtration, precipitation, or a combination thereof; and (5) a crude extract including at least one taxane derived from a yew tree or other source or a crude extract including at least one taxane derived from a plant cell culture extract.

The separation of some taxane compounds is disclosed in U.S. Pat. No. 5,475,120, and J. Org. Chem., Miller R. W. et al., 46:1469-1474 (1981). The taxane separation method disclosed in the documents includes: (1) extracting a dried source (e.g., bark) of paclitaxel with methanol or ethanol and concentrating the resultant extract; (2) extracting the resultant concentrate with dichloromethane or other solvent, followed by concentration, to obtain a powder; (3) dissolving the powder in a solvent and applying the resultant solution to a chromatography column such as a Curosil Florisil column or a silica column; (4) purifying a paclitaxel fraction eluted from the chromatography column by twice crystallization or countercurrent distribution; and (5) applying a pure paclitaxel to a silica column or other chromatography column to perform chromatography.

In addition to the above-described taxane separation method, there are many purification methods for purifying taxane from a natural source. These purification methods are different mainly in terms of the type of an organic solvent used in liquid-phase extraction, a crystallization process, or a pigment removal technique.

According to these conventional taxane separation/purification methods, however, the purity of taxane (in particular, paclitaxel) after primary purification is low, and thus, a purification process must be several times repeated to yield highly purified taxane. Therefore, purification costs are increased, and even when a purification process is repeated several times, the purity of taxane is still low.

According to an embodiment of the present invention, a taxane purification method includes: (1) dissolving a partially purified taxane powder in an appropriate mobile-phase solvent to obtain a taxane-containing solution; (2) applying the taxane-containing solution to a column packed with a cucurbituril-bound silica gel to perform chromatography using an appropriate solvent; (3) collecting an appropriate taxane fraction from the column; (4) removing an organic solvent from the taxane fraction by evaporation under vacuum; and (5) crystallizing and lyophilizing the resultant taxane concentrate. Here, the mobile-phase solvent may be a solvent known in the art.

According to the taxane purification method of the present invention, a taxane with a purity of 95 wt % or more can be yielded. The above-described taxane purification method of the present invention is related to HPLC separation, and subsequent extraction and purification can be performed by methods known in the art. The separation of highly purified taxane from the column can be achieved by good taxane separation capability of the cucurbituril-bound silica gel used as a stationary phase. That is, when a crude taxane extract is allowed to pass through a column packed with a cucurbituril-bound silica gel, the retention time of taxane is distinctly different from that of other components (impurities) due to column characteristics, thereby enabling the separation of taxane from the other components, resulting in highly purified taxane.

The above-described taxane purification method of the present invention can be applied to a taxane mixture with a taxane purity of at least 7 wt % that is partially purified from a taxane source. Most preferably, a taxane compound may be paclitaxel (an effective ingredient in drug Taxol™).

A crude extract (preferably, containing at least 7 wt % of taxane) is dissolved in a mixture of water and methanol or acetonitrile. In order to dissolve the crude extract, other appropriate solvent(s) can also be used. The current embodiment of the present invention has been illustrated with respect to a crude extract containing at least 7 wt % of taxane, but the content of taxane may also be less than 7 wt %.

An appropriate aliquot of a taxane-containing solution is loaded on a cucurbituril-bound silica gel column connected to an appropriate HPLC system. At this time, a loading amount of the taxane-containing solution may vary according to the dimension of the column. The dimension of the column may be as follows: 10-50 cm in length and 2.0-25 mm in diameter, but the present invention is not limited thereto. Any column with an appropriate dimension can also be used.

An HPLC analysis can be performed using a gradient elution program. The present inventors found that the separation of taxane from contaminants was appropriately achieved in an isocratic mode. The isocratic mode may include an eluent of methanol/water, acetonitrile/water, or methanol/acetonitrile/water. In the isocratic mode, methanol may be used in an amount of 45-75 wt %, acetonitrile in an amount of 30-45 wt %, and water in an amount of 25-70 wt %. An eluent is not limited to the above-described mixture of water and methanol and/or acetonitrile. A mixture of water and other appropriate organic solvent(s) can also be effectively used for separation of taxane.

A taxane fraction eluted from a column is subjected to evaporation under vacuum to remove an organic solvent, and precipitated in a residual aqueous phase. Alternatively or preferably, the resultant taxane-containing aqueous phase may be lyophilized.

The extraction of the taxane fraction may be performed on a HPLC column adjusted to 30° C. However, the temperature of the HPLC column can be appropriately changed.

Taxanes interact with cucurbiturils, which enables the separation of taxanes from crude extracts. The present inventors demonstrated a host-guest interaction between cucurbit[7]uril and taxane by $^1$H-NMR spectroscopy.

EMBODIMENTS

Hereinafter, the present invention will be described more specifically with reference to the following working examples. The following working examples are for illustrative purposes and are not intended to limit the scope of the present invention.

Example 1

Synthesis of Cucurbituril-Bound Silica Gel Represented by Formula 5 (n=3)

A cucurbituril-bound silica gel represented by Formula 5 (n=3) below was synthesized by binding a cucurbituril of Formula 1 above wherein X was O, $R_1$'s were each OH, and n was 7, with a silica gel of Formula 3 above wherein $R_2$ was OH, via a silane linker of Formula 4 above wherein $R_3$ was —$OC_2H_5$, Y was NCO, and a was 3:

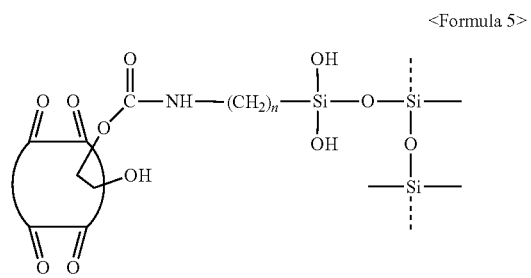

<Formula 5> wherein n is 3.

In detail, the cucurbituril-bound silica gel of Formula 5 above was synthesized as follows.

Hydroxycucurbit[7]uril (6.0 g, 4.33 mmol) was dissolved in anhydrous DMSO (65 ml, Aldrich) in a 250 ml round-bottom flask, and pyridine (7.0 ml) was then added to the flask. Then, 3-(triethoxysilyl)propyl isocyanate (2.35 ml, 9.56 mmol, Aldrich) was added to the flask, and the resultant mixture was incubated at 80° C. for 2 days while sirring under an argon atmosphere. The resultant silylated cucurbit[7]uril intermediate was transferred to a HPLC-grade silica gel (Lichrospher Si 100, particle size of 5 μm, pore size of 100 Å, 2.0 g, dried at 80° C. under vacuum for 24 hours) in a 250 ml round-bottom flask, and the resultant mixture was incubated at 110° C. for 3 days while stirring under an argon atmosphere. The resultant product was several times washed with DMSO, acetone, water, and methanol, and dried under vacuum at 50° C. overnight, to thereby give the cucurbituril-bound silica gel of Formula 5 above.

$^{13}$C—CP MAS: δ(ppm): 162.3, 155.1, 98.6, 44.4, 28.6, 23.5, 14.8.

FT-IR (KBr): 3485, 3150, 2969, 1737, 1467, 1120-1095 cm$^{-1}$.

Example 2

Synthesis of Cucurbituril-Bound Silica Gel Represented by Formula 6 (n=3)

A cucurbituril-bound silica gel represented by Formula 6 (n=3) below was synthesized by binding a cucurbituril of Formula 2 above wherein X was O and R's were each $C_6H_5$—$NH_2$, with a silica gel of Formula 3 above wherein $R_2$ was OH, via a silane linker of Formula 4 above wherein $R_3$ was —$OC_2H_5$, Y was NCO, and a was 3:

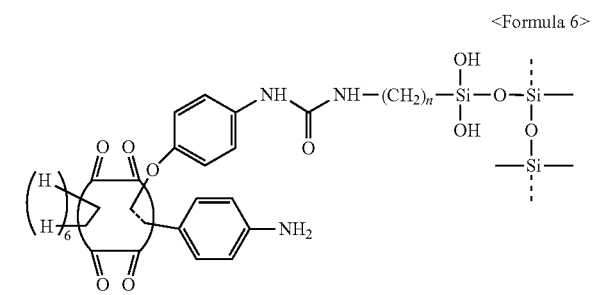

<Formula 6> wherein n is 3.

In detail, the cucurbituril-bound silica gel of Formula 6 above was synthesized as follows.

Di-para-aminophenylcucurbit[7]uril (1.2 g, 0.89 mmol) was dissolved in anhydrous DMSO (30 ml, Aldrich) in a 250 ml round-bottom flask, and pyridine (3.0 ml) was then added to the flask. Then, 3-(triethoxysilyl)propyl isocyanate (0.66 ml, 2.67 mmol, Aldrich) was added to the flask, and the resultant mixture was incubated at 80° C. for 2 days while sirring under an argon atmosphere. The resultant diaminophenylsilylated cucurbit[7]uril intermediate was transferred to a HPLC-grade silica gel (Lichrospher Si 100, particle size of 5 μm, pore size of 100 Å, 0.6 g, dried at 80° C. under vacuum for 24 hours) in a 250 ml round-bottom flask, and the resultant mixture was incubated at 110° C. for 3 days while stirring under an argon atmosphere. The resultant product was several times washed with DMSO, acetone, water, and methanol, and dried under vacuum at 50° C. overnight to thereby give the cucurbituril-bound silica gel of Formula 6 above.

$^{13}$C—CP MAS: δ(ppm): 161.8, 152.5, 133.3, 131.6, 128.9, 121.4, 97.3, 49.6, 27.5, 25.2, 15.3.

FT-IR (KBr): 3450, 3025, 2978, 1737, 1530, 1471, 1100-1090 cm$^{-1}$.

Example 3

Preparation of HPLC Column Using Cucurbituril-Bound Silica Gel

Methanol (50 ml) was added to the cucurbituril-bound silica gel (2.5 g) prepared in Example 1 to make a slurry, and the slurry was then tightly packed into a HPLC steel column (15 cm in length and 0.46 cm in inner diameter, SUPELCO, U.S.A.) using a slurry packing tool. Then, the resultant HPLC steel column was washed with methanol under a pressure of 800 psi for 3 hours prior to HPLC analysis. The HPLC column thus prepared was used as a stationary phase column for HPLC analysis after being attached to a HPLC system.

Example 4

Separation of Paclitaxel from Crude Extract (Paclitaxel Purity: 62.9 Wt %) Derived from Yew Tree Using Cucurbituril-Bound Silica Gel Stationary Phase The separation of paclitaxel from a crude extract (paclitaxel purity: 62.9 wt %) derived from a yew tree was performed using the HPLC column prepared in Example 3. The crude extract was dissolved in a mixture of acetonitrile and water and a 10 μl aliquot of the resultant solution was loaded on the HPLC column. At this time, an eluent (a mixture of acetonitrile and water (35:65, v/v)) was allowed to flow down through the HPLC column at a flow rate of 0.4 ml/min, and an eluate was monitored by a UV detector at 227 nm. The chromatographic results are shown in FIG. 1. The chromatographic results of FIG. 1 show that reverse-phase HPLC analysis can distinctly separate a highly purified paclitaxel peak from impurity peaks.

Example 5

Figure 2:
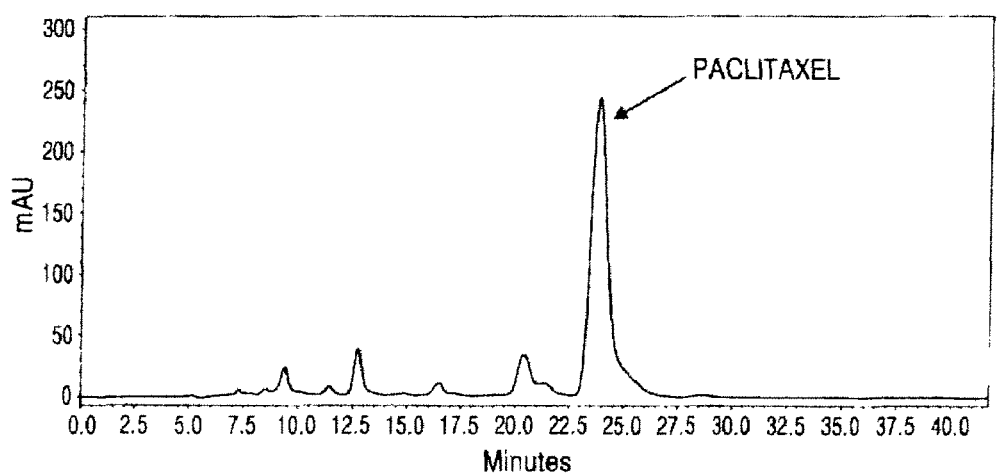
FIG. 2 is an HPLC pattern of paclitaxel separated from a crude extract (paclitaxel purity: 26.6 wt %) derived from a yew tree according to Example 5.

Separation of Paclitaxel from Crude Extract (Paclitaxel Purity: 26.6 Wt %) Derived from Yew Tree Using Cucurbituril-Bound Silica Gel Stationary Phase The separation of paclitaxel from a crude extract (paclitaxel purity: 26.6 wt %) derived from a yew tree was performed using the HPLC column prepared in Example 3. The crude extract was dissolved in a mixture of acetonitrile and water and a 10 μl aliquot of the resultant solution was loaded on the HPLC column. HPLC analysis was performed under the same conditions as in Example 4, and the chromatographic results are shown in FIG. 2. The chromatographic results of FIG. 2 show that reverse-phase HPLC analysis can distinctly separate a highly purified paclitaxel peak from impurity peaks.

Example 6

Figure 3:
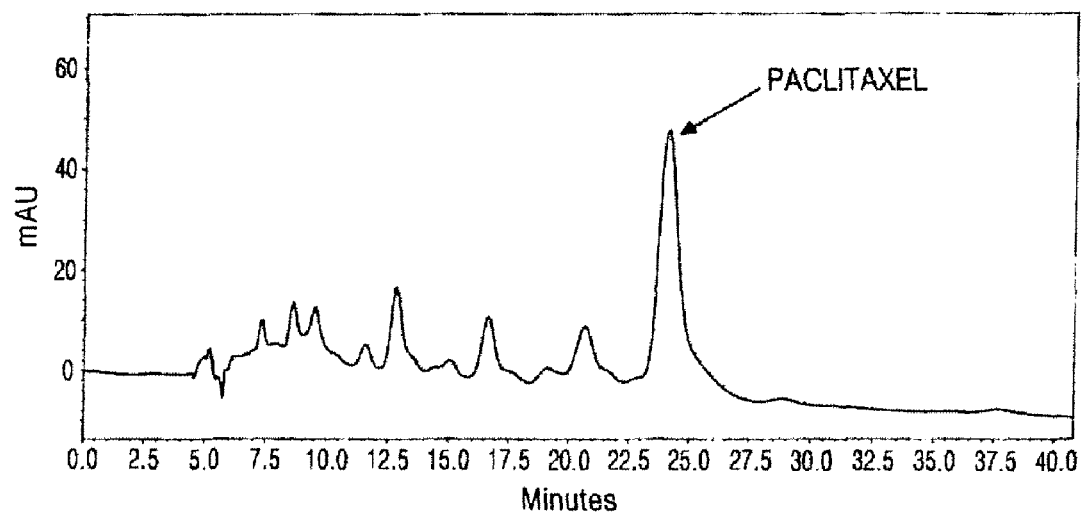
FIG. 3 is an HPLC pattern of paclitaxel separated from a crude extract (paclitaxel purity: 7.1 wt %) derived from a yew tree according to Example 6.

Separation of Paclitaxel from Crude Extract (Paclitaxel Purity: 7.1 Wt %) Derived from Yew Tree Using Cucurbituril-Bound Silica Gel Stationary Phase The separation of paclitaxel from a crude extract (paclitaxel purity: 7.1 wt %) derived from a yew tree was performed using the HPLC column prepared in Example 3. The crude extract was dissolved in a mixture of acetonitrile and water and a 10 μl aliquot of the resultant solution was loaded on the HPLC column. HPLC analysis was performed under the same conditions as in Example 4, and the chromatographic results are shown in FIG. 3. The chromatographic results of FIG. 3 show that reverse-phase HPLC analysis can distinctly separate a highly purified paclitaxel peak from impurity peaks.

Example 7

Figure 4:
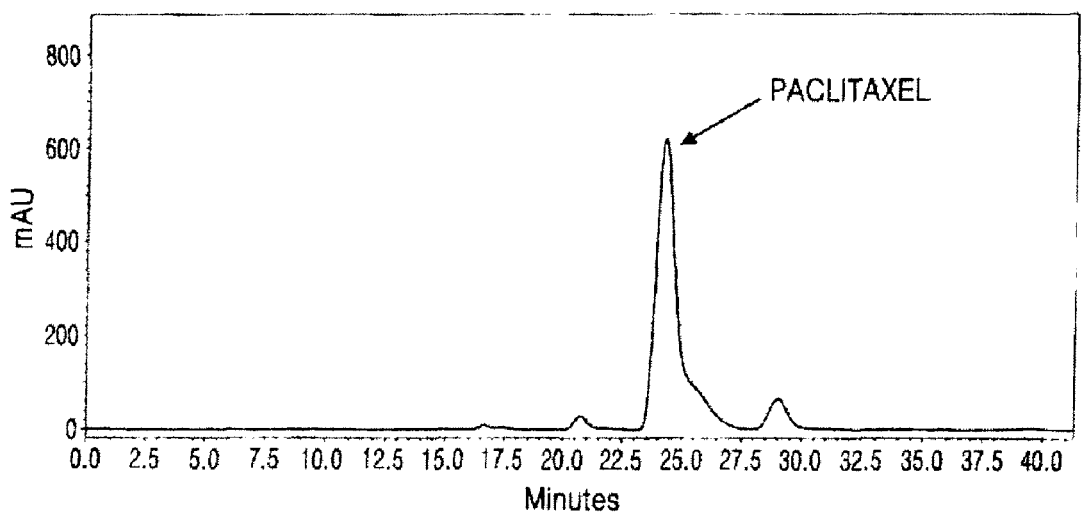
FIG. 4 is an HPLC pattern of paclitaxel separated from a crude extract (paclitaxel purity: 51.6 wt %) derived from a cell culture according to Example 7.

Separation of Paclitaxel from Crude Extract (Paclitaxel Purity: 51.6 Wt %) Derived from Cell Culture Using Cucurbituril-Bound Silica Gel Stationary Phase The separation of paclitaxel from a crude extract (paclitaxel purity: 51.6 wt %) derived from a cell culture was performed using the HPLC column prepared in Example 3. The crude extract was dissolved in a mixture of acetonitrile and water and a 10 μl aliquot of the resultant solution was loaded on the HPLC column. HPLC analysis was performed under the same conditions as in Example 4, and the chromatographic results are shown in FIG. 4. The chromatographic results of FIG. 4 show that reverse-phase HPLC analysis can distinctly separate a highly purified paclitaxel peak from impurity peaks.

Example 8

Figure 5:
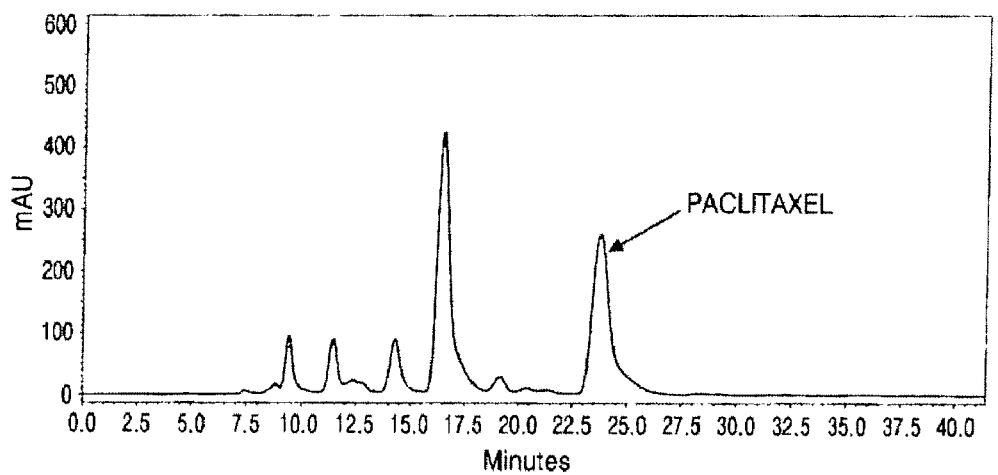
FIG. 5 is an HPLC pattern of paclitaxel separated from a crude extract (paclitaxel purity: 19.3 wt %) derived from a cell culture according to Example 8.

Separation of Paclitaxel from Crude Extract (Paclitaxel Purity: 19.3 Wt %) Derived from Cell Culture Using Cucurbituril-Bound Silica Gel Stationary Phase The separation of paclitaxcel from a crude extract (paclitaxel purity: 19.3 wt %) derived from a cell culture was performed using the HPLC column prepared in Example 3. The crude extract was dissolved in a mixture of acetonitrile and water and a 10 μl aliquot of the resultant solution was loaded on the HPLC column. HPLC analysis was performed under the same conditions as in Example 4, and the chromatographic results are shown in FIG. 5. The chromatographic results of FIG. 5 show that reverse-phase HPLC analysis can distinctly separate a highly purified paclitaxel peak from impurity peaks.

Comparative Example 1

Figure 6:
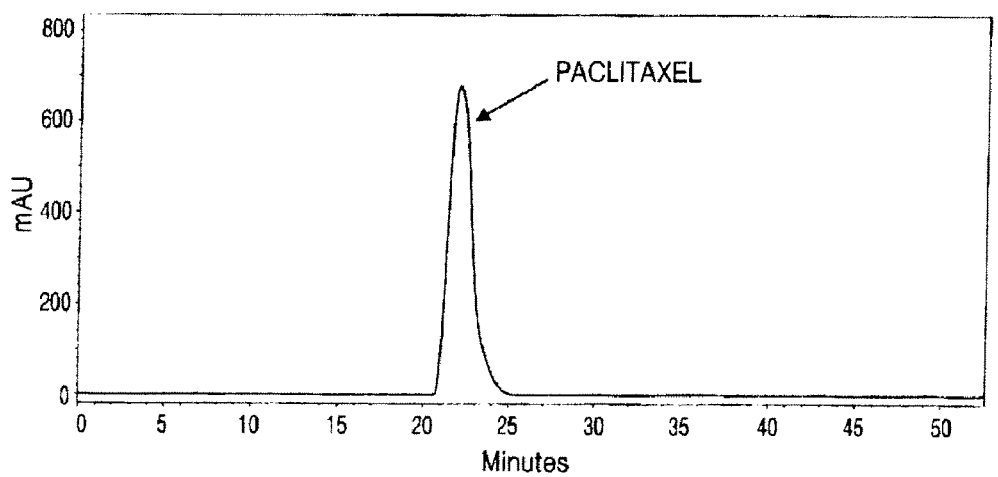
FIG. 6 is an HPLC pattern of pure paclitaxel (99.9 wt %) according to Comparative Example 1.

Separation of Pure Paclitaxel (Purity: 99.9 Wt %) Using Cucurbituril-Bound Silica Gel Stationary Phase The analysis of pure paclitaxel (purity: 99.9 wt %) was performed using the HPLC column prepared in Example 3. The pure paclitaxel was dissolved in a mixture of acetonitrile and water and a 10 μl aliquot of the resultant solution was loaded on the HPLC column. HPLC analysis was performed under the same conditions as in Example 4, and the chromatographic results are shown in FIG. 6. Based on the position of a paclitaxel peak of Comparative Example 1 as shown in FIG. 6, the positions of paclitaxel peaks of the other working examples of the present invention can be determined.

Example 9

Preparation of HPLC Column Using Diaminophenylcucurbituril-Bound Silica Gel

Methanol (55 ml) was added to the diaminophenylcucurbituril-bound silica gel (2.6 g) prepared in Example 2 to make a slurry, and the slurry was then tightly packed into a HPLC steel column (15 cm in length and 0.46 cm in inner diameter, SUPELCO, U.S.A.) using a slurry packing tool. Then, the resultant HPLC steel column was washed with methanol under a pressure of 800 psi for 3 hours prior to HPLC analysis. The HPLC column thus prepared was used as a stationary phase column for HPLC analysis after being attached to a HPLC system.

Example 10

Figure 7:
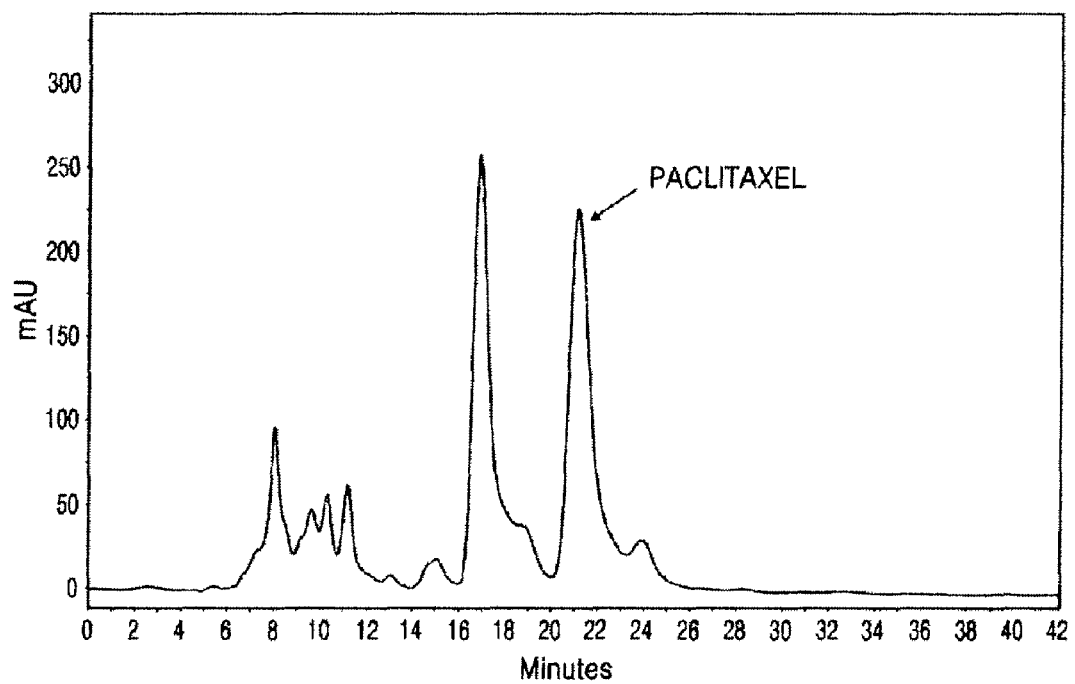
FIG. 7 is an HPLC pattern of paclitaxel separated from a crude extract (paclitaxel purity: 19.3 wt %) derived from a cell culture according to Example 10.

Separation of Paclitaxel from Crude Extract (Paclitaxel Purity: 19.3 Wt %) Derived from Cell Culture Using Diaminophenylcucurbituril-Bound Silica Gel Stationary Phase The separation of paclitaxel from a crude extract (paclitaxel purity: 19.3 wt %) derived from a cell culture was performed using the HPLC column prepared in Example 9. The crude extract was dissolved in a mixture of acetonitrile and water and a 10 μl aliquot of the resultant solution was loaded on the HPLC column. HPLC analysis was performed under the same conditions as in Example 4, and the chromatographic results are shown in FIG. 7. The chromatographic results of FIG. 7 show that reverse-phase HPLC analysis can distinctly separate a highly purified paclitaxel peak from impurity peaks.

Example 11

$^1$H-NMR Analysis of Cucurbit[7]uril-Bound Paclitaxel

Figure 8:
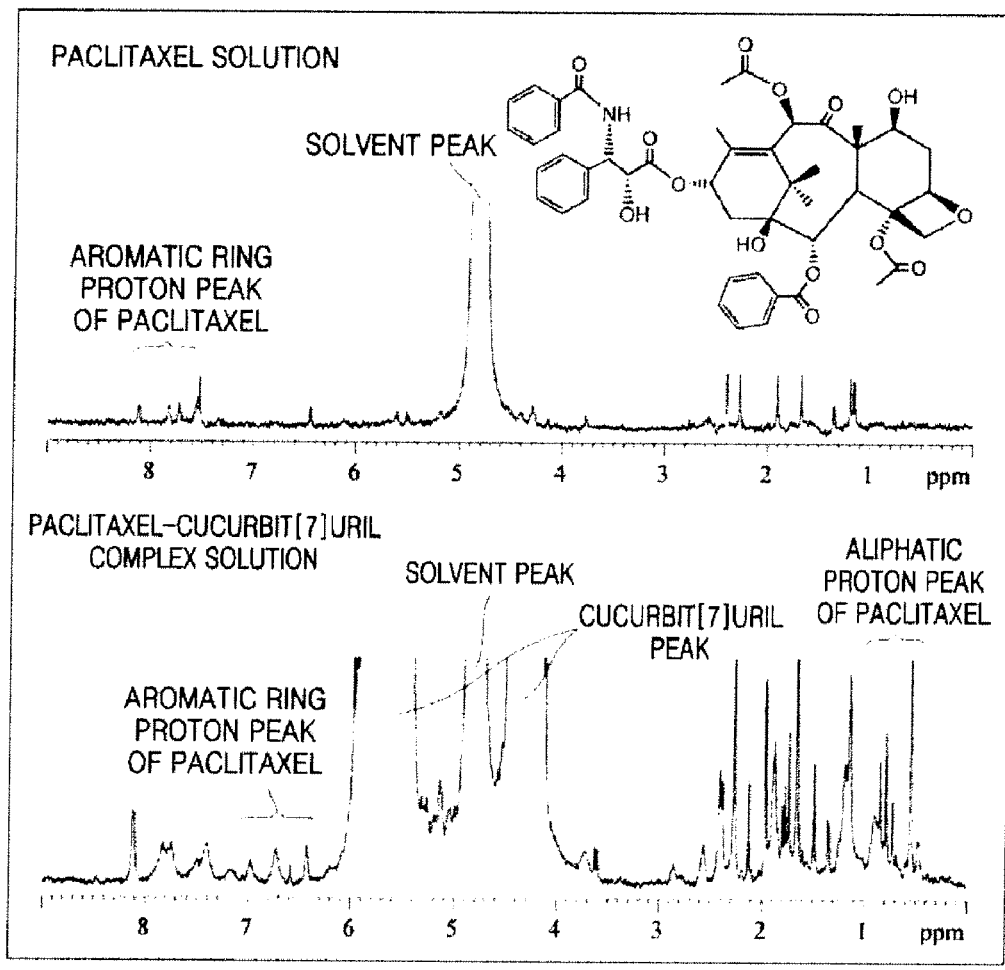
FIG. 8 is a $^1$H-NMR spectrum of paclitaxel that forms a paclitaxel-cucurbit[7]uril complex in deuterated water ($D_2O$) according to Example 11.

Pure paclitaxel (4 mg) was dissolved in $D_2O$ (1 ml), and cucurbit[7]uril (10 mg) was then added thereto. $^1$H-NMR analysis of a cucurbituril-paclitaxel complex wherein paclitaxel molecules were partially trapped in cucurbit[7]uril molecules was performed at room temperature by $^1$H-NMR spectroscopy to investigate a host-guest interaction between cucurbit[7]uril and paclitaxel, and the results are shown in FIG. 8. In FIG. 8, an upper $^1$H-NMR spectrum is for a paclitaxel solution, and a lower $^1$H-NMR spectrum is for a paclitaxel-cucurbit[7]uril solution. Referring to FIG. 8, aromatic ring proton peaks derived from $C_6H_5$—CO of paclitaxel in the paclitaxel solution were observed in 7.45-8.15 ppm range. These aromatic ring protons were shifted upfield (6.35-7.05 ppm range) after an interaction between paclitaxel and cucurbit[7]uril occurred. This shows that paclitaxel molecules are trapped in cucurbit[7]uril molecules. After forming a cucurbit[7]uril-paclitaxel complex, aliphatic proton peaks of paclitaxel were observed in 0.4-1.0 ppm range. This shows that the aliphatic groups of paclitaxel interact with cucurbit[7]uril.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:
1. A method of separating taxane, the method comprising:
preparing a column for taxane separation, the column being packed with a stationary phase comprising a cucurbituril-bound silica gel in which a cucurbituril represented by Formula 1 or 2 below is covalently bound to a modified silica gel represented by Formula 3 below;
dissolving a taxane powder in a solvent to prepare a taxane-containing solution;
applying the taxane-containing solution to the column;
supplying a mobile-phase solvent to the column to obtain a taxane extract from the column; and
purifying taxane from the taxane extract:

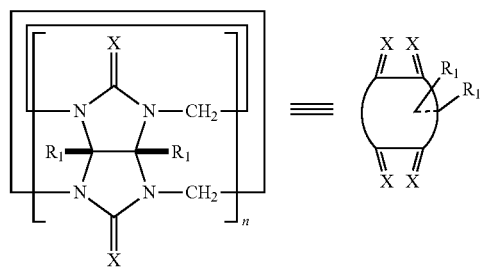

(1)

wherein at least one of $R_1$'s is selected from the group consisting of hydrogen, a hydroxy group, a substituted or unsubstituted alkyloxy group of C1-C30, a substituted or unsubstituted alkenyloxy group of C1-C30, a substituted or unsubstituted alkynyloxy group of C1-C30, a substituted or unsubstituted carbonylalkyloxy group of C2-C30, a substituted or unsubstituted thioalkyloxy group of C1-C30, a substituted or unsubstituted alkylthioloxy group of C1-C30, a substituted or unsubstituted hydroxyalkyloxy group of C1-C30, a substituted or unsubstituted alkylsiloxy group of C1-C30, a substituted or unsubstituted aminoalkyloxy group of C1-C30, a substituted or unsubstituted aminoalkylthiolalkyloxy group of C1-C30, a substituted or unsubstituted cycloalkyloxy group of C5-C30, a substituted or unsubstituted heterocycloalkyloxy group of C2-C30, a substituted or unsubstituted aryloxy group of C6-C30, a substituted or unsubstituted arylalkyloxy group of C6-C20, a substituted or unsubstituted heteroaryloxy group of C4-C30, a substituted or unsubstituted heteroarylalkyloxy group of C4-C30, a substituted or unsubstituted alkylthio group of C1-C30, a substituted or unsubstituted alkenylthio group of C1-C30, a substituted or unsubstituted alkynylthio group of C1-C30, a substituted or unsubstituted carbonylalkylthio group of C2-C30, a substituted or unsubstituted thioalkylthio group of C1-C30, a substituted or unsubstituted hydroxyalkylthio group of C1-C30, a substituted or unsubstituted alkylsilylthio group of C1-C30, a substituted or unsubstituted aminoalkylthio group of C1-C30, a substituted or unsubstituted aminoalkylthiolalkylthio group of C1-C30, a substituted or unsubstituted cycloalkylthio group of C5-C30, a substituted or unsubstituted heterocycloalkylthio group of C2-C30, a substituted or unsubstituted arylthio group of C6-C30, a substituted or unsubstituted arylalkylthio group of C6-C20, a substituted or unsubstituted heteroarylthio group of C4-C30, a substituted or unsubstituted heteroarylalkylthio group of C4-C30, a substituted or unsubstituted alkylamine group of C1-C30, a substituted or unsubstituted alkenylamine group of C1-C30, a substituted or unsubstituted alkynylamine group of C1-C30, a substituted or unsubstituted carbonylalkylamine group of C2-C30, a substituted or unsubstituted thioalkylamine group of C1-C30, a substituted or unsubstituted hydroxyalkylamine group of C1-C30, a substituted or unsubstituted alkylsilylamine group of C1-C30, a substituted or unsubstituted trialkyloxysilyl alkyl-carbamate group of C1-C30, a substituted or unsubstituted trialkyloxysilyl alkyl-thiocarbamate group of C1-C30, a substituted or unsubstituted trialkyloxysilyl alkyloxy group of C1-C30, a substituted or unsubstituted trialkyloxysilyl alkyl-carbonyloxy group of C1-C30, a substituted or unsubstituted trialkyloxysilyl heteroalkyl-alkyloxy group of C1-C30, a substituted or unsubstituted aminoalkylamine group of C1-C30, a substituted or unsubstituted aminoalkylthiolalkylamine group of C1-C30, a substituted or unsubstituted cycloalkylamine group of C5-C30, a substituted or unsubstituted heterocycloalkylamine group of C2-C30, a substituted or unsubstituted arylamine group of C6-C30, a substituted or unsubstituted arylalkylamine group of C6-C20, a substituted or unsubstituted heteroarylamine group of C4-C30, a substituted or unsubstituted heteroarylalkylamine group of C4-C30, a substituted or unsubstituted alkylazide group of C1-C30, a substituted or unsubstituted arylazide group of C1-C30, a substituted or unsubstituted alkylcarboxylazide group of C1-C30, and a substituted or unsubstituted arylcarboxylazide group of C1-C30;

X is O, S, or NH; and n is an integer of 4 to 20,

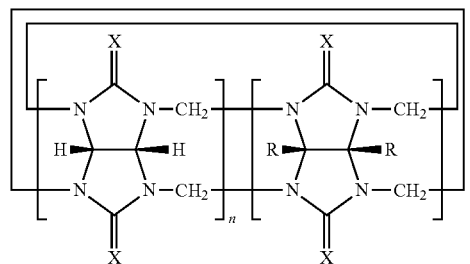

(2)

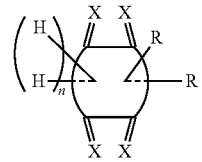

wherein at least one of R's is selected from the group consisting of hydrogen, a hydroxy group, a substituted or unsubstituted alkyloxy group of C1-C30, a substituted or unsubstituted alkenyloxy group of C1-C30, a substituted or unsubstituted alkynyloxy group of C1-C30, a substituted or unsubstituted carbonylalkyloxy group of C2-C30, a substituted or unsubstituted thioalkyloxy group of C1-C30, a substituted or unsubstituted alkylthioloxy group of C1-C30, a substituted or unsubstituted hydroxyalkyloxy group of C1-C30, a substituted or unsubstituted alkylsiloxy group of C1-C30, a substituted or unsubstituted aminoalkyloxy group of C1-C30, a substituted or unsubstituted aminoalkylthiolalkyloxy group of C1-C30, a substituted or unsubstituted cycloalkyloxy group of C5-C30, a substituted or unsubstituted heterocycloalkyloxy group of C2-C30, a substituted or unsubstituted aryloxy group of C6-C30, a substituted or unsubstituted arylalkyloxy group of C6-C20, a substituted or unsubstituted heteroaryloxy group of C4-C30, a substituted or unsubstituted heteroarylalkyloxy group of C4-C30, a substituted or unsubstituted alkylthio group of C1-C30, a substituted or unsubstituted alkenylthio group of C1-C30, a substituted or unsubstituted alkynylthio group of C1-C30, a substituted or unsubstituted carbonylalkylthio group of C2-C30, a substituted or unsubstituted thioalkylthio group of C1-C30, a substituted or unsubstituted hydroxyalkylthio group of C1-C30, a substituted or unsubstituted alkylsilylthio group of C1-C30, a substituted or unsubstituted aminoalkylthio group of C1-C30, a substituted or unsubstituted aminoalkylthiolalkylthio group of C1-C30, a substituted or unsubstituted cycloalkylthio group of C5-C30, a substituted or unsubstituted heterocycloalkylthio group of C2-C30, a substituted or unsubstituted arylthio group of C6-C30, a substituted or unsubstituted arylalkylthio group of C6-C20, a substituted or unsubstituted heteroarylthio group of C4-C30, a substituted or unsubstituted heteroarylalkylthio group of C4-C30, a substituted or unsubstituted alkylamine group of C1-C30, a substituted or unsubstituted alkenylamine group of C1-C30, a substituted or unsubstituted alkynylamine group of C1-C30, a substituted or unsubstituted carbonylalkylamine group of C2-C30, a substituted or unsubstituted thioalkylamine group of C1-C30, a substituted or unsubstituted hydroxyalkylamine group of C1-C30, a substituted or unsubstituted alkylsilylamine group of C1-C30, a substituted or unsubstituted trialkyloxysilyl alkyl-carbamate group of C1-C30, a substituted or unsubstituted trialkyloxysilyl alkyl-thiocarbamate group of C1-C30, a substituted or unsubstituted trialkyloxysilyl alkyloxy group of C1-C30, a substituted or unsubstituted trialkyloxysilyl alkyl-carbonyloxy group of C1-C30, a substituted or unsubstituted trialkyloxysilyl heteroalkyl-alkyloxy group of C1-C30, a substituted or unsubstituted aminoalkylamine group of C1-C30, a substituted or unsubstituted aminoalkylthiolalkylamine group of C1-C30, a substituted or unsubstituted cycloalkylamine group of C5-C30, a substituted or unsubstituted heterocycloalkylamine group of C2-C30, a substituted or unsubstituted arylamine group of C6-C30, a substituted or unsubstituted arylalkylamine group of C6-C20, a substituted or unsubstituted heteroarylamine group of C4-C30, a substituted or unsubstituted heteroarylalkylamine group of C4-C30, a substituted or unsubstituted alkylazide group of C1-C30, a substituted or unsubstituted arylazide group of C1-C30, a substituted or unsubstituted alkylcarboxylazide group of C1-C30, and a substituted or unsubstituted arylcarboxylazide group of C1-C30;

X is O, S, or NH; and n is an integer of 3 to 19, and

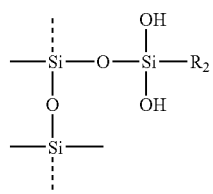

(3)

wherein $R_2$ is an alkylthiol group with an alkyl moiety of C2-C10, an alkylamine group with an alkyl moiety of C2-C10, an epoxyalkyloxyalkyl group with an alkyl moiety of C2-C10, an isocyanatoalkyl group with an alkyl moiety of C2-C10, a halogenated alkyl group with an alkyl moiety of C2-C10, or a hydroxy group.

2. The method of claim 1, wherein in preparation of the column for taxane separation, the cucurbituril-bound silica gel is synthesized by binding the cucurbituril of Formula 1 or 2 with the modified silica gel of Formula 3 via a silane linker represented by Formula 4 below:

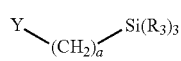

(4)

wherein Y is selected from the group consisting of a thiol group, an amino group, an epoxy group, an isocyanate group, an isothiocyanate group, a hydroxy group, a carboxylated halogen, an azide group, an alkenyloxy group, a carbonylalkyloxy group, a thioalkyloxy group, an alkylthioloxy group, a hydroxyalkyloxy group, an alkylsilyloxy group, an aminoalkyloxy group, an aminoalkylthiolalkyloxy group, a cycloalkyloxy group, a heterocycloalkyloxy group, an aryloxy group, an arylalkyloxy group, a heteroaryloxy group, a heteroarylalkyloxy group, an alkylthio group, an alkenylthio group, an alkynylthio group, a carbonylalkylthio group, a thioalkylthio group, a hydroxyalkylthio group, an alkylsilylthio group, an aminoalkylthio group, an aminoalkylthiolalkylthio group, a cycloalkylthio group, a heterocycloalkylthio group, an arylthio group, an arylalkylthio group, a heteroarylthio group, a heteroarylalkylthio group, an alkylamine group, an alkenylamine group, an alkynylamine group, a carbonylalkylamine group, a thioalkylamine group, a hydroxyalkylamine group, an alkylsilylamine group, an aminoalkylamine group, an aminoalkylthiolalkylamine group, a cycloalkylamine group, a heterocycloalkylamine group, an arylamine group, an arylalkylamine group, a heteroarylamine group, and a heteroarylalkylamine group;

a is an integer of 1 to 10; and $R_3$ is selected from the group consisting of hydrogen, a halogen atom, an allyl group, an alkyl group of C1-C20, a halogenated alkyl group of C1-C20, and an alkyloxy group of C1-C20.

3. The method of claim 1, wherein in Formula 4, $R_3$ is —$OC_2H_5$, Y is NCO, and a is 3.

4. The method of claim 1, wherein the cucurbituril-bound silica gel is represented by Formula 5 or 6 below:

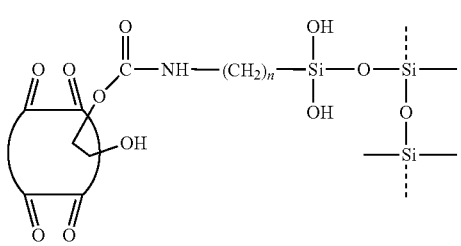

(5)

wherein n is an integer of 4 to 20, and

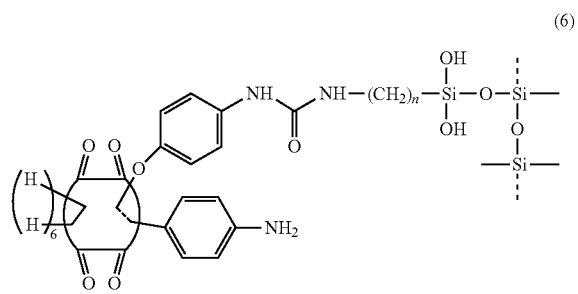

(6)

wherein n is an integer of 4 to 20.

5. The method of claim 4, wherein in Formulae 5 and 6, n is 3.

6. The method of claim 1, wherein the purification of the taxane from the taxane extract comprises:

distilling the taxane extract under vacuum to obtain an organic solvent-free taxane concentrate; and crystallizing the taxane concentrate.

7. The method of claim 6, wherein the purification of the taxane from the taxane extract further comprises lyophilizing the taxane concentrate after the crystallization.

8. The method of claim 1, wherein in Formula 1, at least one of $R_1$'s is selected from the group consisting of hydrogen, a hydroxy group, an aminophenyl group, an allyoxy group, a halomethyl group, and an aminoalkyl group of C1-C10, X is O, and n is 7.

9. The method of claim 8, wherein the halomethyl group is a bromomethyl group, a fluoromethyl group, or an iodomethyl group.

10. The method of claim 1, wherein in Formula 1, $R_1$'s are each a hydroxy group.

11. The method of claim 1, wherein in Formula 2, at least one of R's is selected from the group consisting of hydrogen, a hydroxy group, an aminophenyl group, an allyoxy group, a halomethyl group, and an aminoalkyl group of C1-C10, X is O, and n is 6.

12. The method of claim 11, wherein the halomethyl group is a bromomethyl group, a fluoromethyl group, or an iodomethyl group.

13. The method of claim 1, wherein in Formula 2, R's are each $C_6H_5-NH_2$.

14. The method of claim 1, wherein in Formula 3, $R_2$ is a hydroxy group.

* * * * *